(12) United States Patent
Westlund et al.

(10) Patent No.: US 8,513,292 B2
(45) Date of Patent: Aug. 20, 2013

(54) COMPOSITIONS AND METHODS FOR THE TREATMENT OF CANCER

(75) Inventors: Neil Westlund, Groton, MA (US); Jason Hill, Auburndale, MA (US); Mark A. Ashwell, Carlisle, MA (US); Nivedita Namdev, Westford, MA (US); Jianqiang Wang, Acton, MA (US); Syed Ali, North Andover, MA (US)

(73) Assignee: ArQule, Inc., Woburn, MA (US)

( * ) Notice: Subject to any disclaimer, the term of this patent is extended or adjusted under 35 U.S.C. 154(b) by 587 days.

(21) Appl. No.: 12/664,345
(22) PCT Filed: Jun. 19, 2008
(86) PCT No.: PCT/US2008/067566
§ 371 (c)(1),
(2), (4) Date: Mar. 19, 2010
(87) PCT Pub. No.: WO2009/002807
PCT Pub. Date: Dec. 31, 2008

(65) Prior Publication Data
US 2010/0183603 A1   Jul. 22, 2010

Related U.S. Application Data
(60) Provisional application No. 60/945,820, filed on Jun. 22, 2007.

(51) Int. Cl.
*A61K 31/437*  (2006.01)
*C07D 221/06*  (2006.01)
*C07D 471/06*  (2006.01)

(52) U.S. Cl.
USPC ............ 514/394; 514/411; 546/94; 548/428

(58) Field of Classification Search
USPC .................... 514/294, 411; 548/428; 546/94
See application file for complete search history.

(56) References Cited

U.S. PATENT DOCUMENTS

| 4,522,811 A | 6/1985 | Eppstein et al. ............ 514/2 |
| 5,057,614 A | 10/1991 | Davis et al. ............... 548/466 |

(Continued)

FOREIGN PATENT DOCUMENTS

| EP | 0384349 | 8/1990 |
| EP | 0397060 | 11/1990 |

(Continued)

OTHER PUBLICATIONS

Cancer Drug Design and Discovery Neidle, Stephen, ed. (Elsevier/Academic Press, 2008) p. 427-431.*

(Continued)

*Primary Examiner* — Jason M Nolan
(74) *Attorney, Agent, or Firm* — Sunstein Kann Murphy & Timbers LLP

(57) ABSTRACT

The present invention relates to pyrrolidine-2,5-dione compounds, and methods of preparation of these compounds. The present invention also relates to pharmaceutical compositions comprising pyrrolidine-2,5-dione compounds. The present invention provides methods of treating a cell proliferative disorder, such as a cancer, by administering to a subject in need thereof a therapeutically effective amount of a compound or pyrrolidine-2,5-dione compound of the present invention. (Ia) (Ib) (IIa) (IIIb) Where U is independently selected from: (I) or (II)

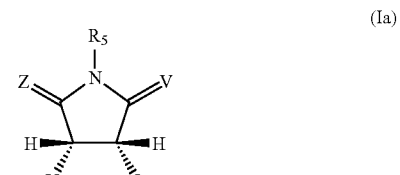

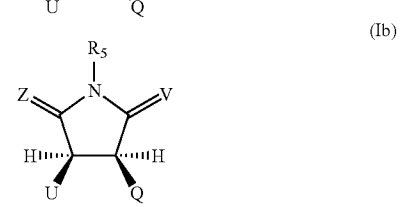

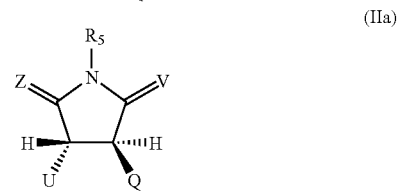

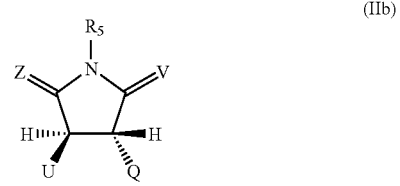

where U is independently selected from:

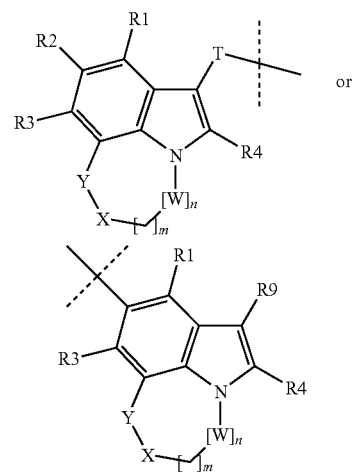

26 Claims, 1 Drawing Sheet

(56) References Cited

U.S. PATENT DOCUMENTS

| | | | |
|---|---|---|---|
| 5,292,747 A | 3/1994 | Davis et al. | 514/285 |
| 5,380,746 A | 1/1995 | Barth et al. | 514/414 |
| 5,516,915 A | 5/1996 | Barth et al. | 548/455 |
| 5,545,636 A | 8/1996 | Heath, Jr. et al. | 514/214 |
| 5,559,228 A | 9/1996 | Gillig et al. | 540/460 |
| 5,591,842 A | 1/1997 | Kojiri et al. | 536/27.1 |
| 5,591,855 A | 1/1997 | Hudkins et al. | 546/256 |
| 5,721,230 A | 2/1998 | Harris et al. | 514/214 |
| 5,721,245 A | 2/1998 | Davis et al. | 514/294 |
| 5,856,517 A | 1/1999 | Huryn et al. | 548/455 |
| 5,859,261 A | 1/1999 | Faul et al. | 548/466 |
| RE36,736 E | 6/2000 | Davis et al. | 548/466 |
| 6,153,641 A | 11/2000 | Bergstrand et al. | 514/414 |
| 6,524,832 B1 | 2/2003 | Kufe et al. | 435/173.1 |
| 6,867,198 B2 | 3/2005 | Al-Awar et al. | 514/44 |
| 7,070,968 B2 | 7/2006 | Kufe et al. | 435/173.1 |
| 7,713,969 B2 * | 5/2010 | Li et al. | 514/233.2 |
| 2006/0251734 A1 | 11/2006 | Kufe et al. | 424/649 |

FOREIGN PATENT DOCUMENTS

| | | |
|---|---|---|
| EP | 0825190 | 2/1998 |
| EP | 1120414 | 8/2001 |
| WO | WO 91/13070 | 9/1991 |
| WO | WO 91/13071 | 9/1991 |
| WO | WO 93/18765 | 9/1993 |
| WO | WO 95/17182 | 6/1995 |
| WO | WO 95/30682 | 11/1995 |
| WO | WO 97/34890 | 9/1997 |
| WO | WO 98/04551 | 2/1998 |
| WO | WO 98/04552 | 2/1998 |
| WO | WO 98/16528 | 4/1998 |
| WO | WO 00/47575 | 8/2000 |
| WO | WO 01/44235 | 6/2001 |
| WO | WO 01/44247 | 6/2001 |
| WO | WO 01/74807 | 10/2001 |
| WO | WO 02/02593 | 1/2002 |
| WO | WO 03/066808 | 8/2003 |
| WO | WO 03/076442 | 9/2003 |
| WO | WO 2004/091548 | 10/2004 |
| WO | WO 2004/096224 | 11/2004 |
| WO | WO 2005/001486 | 1/2005 |
| WO | WO 2005/007193 | 1/2005 |
| WO | WO 2005/058965 | 6/2005 |
| WO | WO 2006/086484 | 8/2006 |
| WO | WO 2006/086484 A1 * | 8/2006 |
| WO | WO 2006/105511 | 10/2006 |
| WO | WO 01/85685 | 11/2011 |

OTHER PUBLICATIONS

Al-awar et al., "1,7 Annulated indolocarbazoles as cyclin-dependent kinase inhibitors," Bioorganic & Medicinal Chemistry Letters, vol. 14, pp. 3217-3220, 2004.

Davis et al., "Inhibitors of Protein Kinase C. 1. 2,3-Bisarylmaleimides," J. Med. Chem., vol. 35, pp. 177-184, 1992.

Li et al., "An Improved Protocol for the Preparation of 3-Pyridyl-and Some Arylboronic Acids," J. Org. Chem., vol. 67, pp. 5394-5397, 2002.

Marson et al., "Highly efficient syntheses of 3-aryl-2-cycloalken-1-ones and an evaluation of their liquid crystalline properties," Tetrahedron, vol. 59, pp. 4377-4381, 2003.

Sancelme et al., "Antimicrobial Activities of Indolocarbazole and Bis-indole Protein Kinase C Inhibitors," The Journal of Antibiotics, vol. 47, No. 7, pp. 792-798, Jul. 1994.

Slater et al., "Indolocarbazoles: Potent, Selective Inhibitors of Human Cytomegalovirus Replication," Bioorganic & Med. Chem., vol. 7, pp. 1067-1074, 1999.

Walker, "Staurosporine: Discovery of a potential anti-cancer drug?" http://freespace.virgin.net/clive.walker1/staurosporine/staurosporine2.html, Dec. 2001.

Al-awar et al., Synthesis of 1,7-annulated indoles and their applications in the studies of cyclin dependent kinase inhibitors, Bioorganic & Medicinal Chemistry Letters, vol. 14, pp. 3057-3061, 2004.

International Searching Authority, International Search Report—International Application No. PCT/US2006/004456, dated Jul. 5, 2006, together with the Written Opinion of the International Searching Authority, 13 pages.

International Searching Authority, International Search Report—International Application No. PCT/US2008/067566, dated Jun. 18, 2009, together with the Written Opinion of the International Searching Authority, 16 pages.

International Searching Authority, International Search Report—International Application No. PCT/US2008/067564, dated Oct. 10, 2008, together with the Written Opinion of the International Searching Authority, 14 pages.

European Patent Office, Extended European Search Report, Application No. 10172543.0-2117, dated Dec. 23, 2010, 5 pages.

European Patent Office, Extended European Search Report, Application No. 11170218.9-2117, dated Nov. 8, 2011, 7 pages.

* cited by examiner

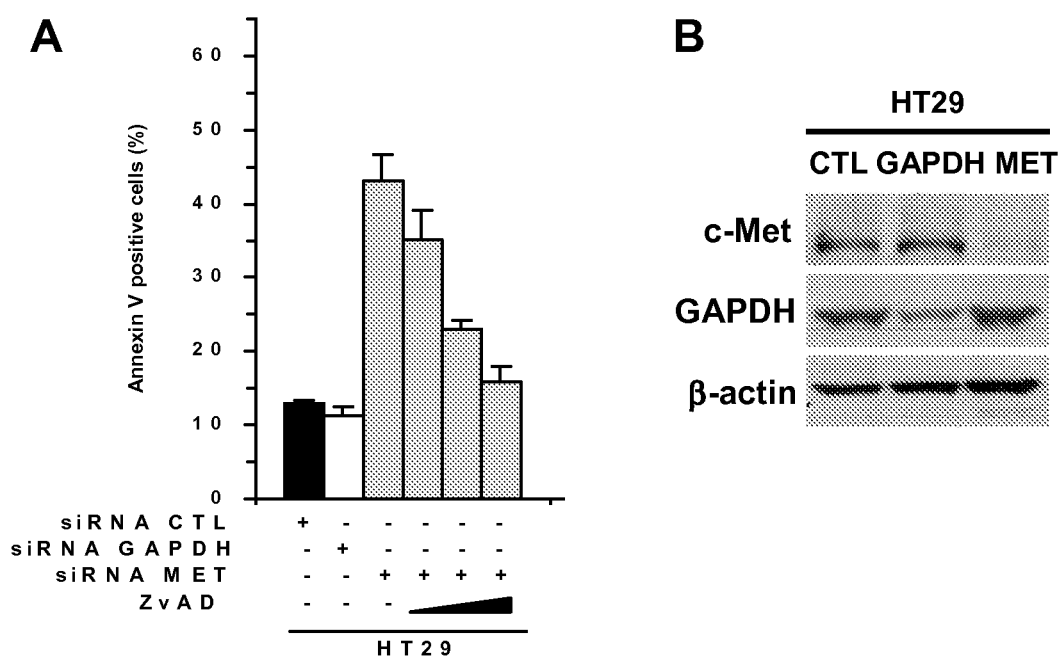

COMPOSITIONS AND METHODS FOR THE TREATMENT OF CANCER

CROSS-REFERENCE TO RELATED APPLICATIONS

This application claims the benefit of U.S. Provisional Applications No. 60/945,820, filed Jun. 22, 2007, the contents of which are incorporated herein by reference in their entirety.

BACKGROUND OF THE INVENTION

Cancer is the second leading cause of death in the United States, exceeded only by heart disease. (*Cancer Facts and Figures* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same type that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine,* 5th Edition, Bast et al. eds., B.C. Decker Inc., Hamilton, Ontario)

Breast cancer is the most frequently diagnosed non-skin cancer in women, and ranks second among cancer deaths in women, after lung cancer. (*Cancer Facts and Figures* 2004, American Cancer Society, Inc.) Current treatment options for breast cancer include surgery, radiotherapy, and chemotherapy/hormone therapy with agents such as tamoxifen, aromatase inhibitors, HERCEPTIN® (trastuzumab), TAXOL® (paclitaxel), cyclophosphamide, methotrexate, doxorubicin (adriamycin), and 5-fluoruracil. Despite improvements in cancer diagnostics and therapeutics, breast cancer incidence rates have continued to increase since 1980. In 2004, about 215,000 new cases of breast cancer were expected in women, and about 1,450 new cases of breast cancer are expected in men. Id. Accordingly, new compounds and methods for treating breast cancer are needed.

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and over-expression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are expressed in numerous tissues, and their expression is normally confined predominantly to cells of epithelial and mesenchymal origin, respectively. c-Met and HGF are dysregulated in human cancers, and may contribute to dysregulation of cell growth, tumor cell dissemination, and tumor invasion during disease progression and metastasis. (See, e.g., *Journal of Clinical Investigation* 109: 863-867 (2002) and *Cancer Cell* pp 5-6 Jul. 2004) c-Met and HGF are highly expressed relative to surrounding tissue in numerous cancers, and their expression correlates with poor patient prognosis. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)). Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003)).

WO 2006/086484 discloses pyrrole-2,5-dione compounds and pyrrolidine-2,5-dione compounds, and methods of preparation of these compounds. The compounds are capable of selectively inhibiting the activity of c-Met, and can be used to treat a cell proliferative disorder, such as a cancer. There is a need for the development of more c-Met inhibitors for the treatment of cancer.

The references cited herein are not admitted to be prior art to the claimed invention.

SUMMARY OF THE INVENTION

The present invention provides a compound of formula Ia, Ib, IIa, or IIb, or pharmaceutically acceptable salts thereof:

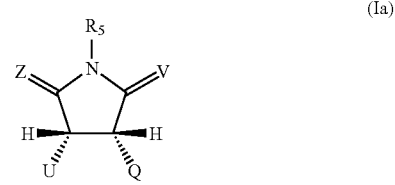

(Ia)

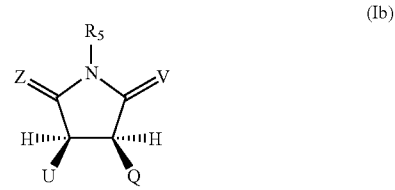

(Ib)

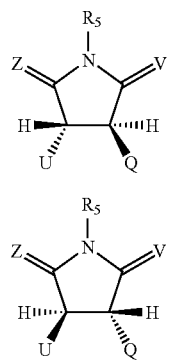

(IIa)

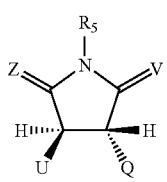

(IIb)

Where U is independently selected from:

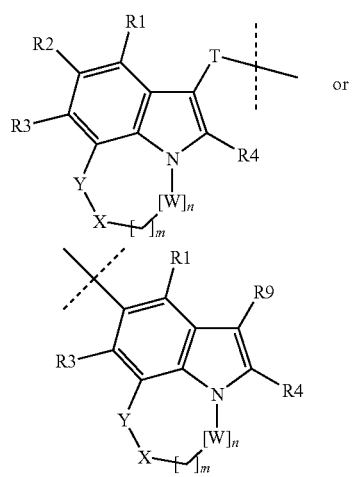

wherein:

R1, R2, and R3 are independently selected from the group consisting of H, F, Cl, Br, I, —NR7R8, —($C_1$-$C_6$)alkyl, —($C_1$-$C_6$) substituted alkyl, —($C_3$-$C_9$)cycloalkyl, —($C_3$-$C_9$) substituted cycloalkyl, —O—($C_1$-$C_6$) alkyl, —O—($C_3$-$C_9$) cycloalkyl, and —O—($C_3$-$C_9$) substituted cycloalkyl, aryl, heteroaryl, and heterocyclyl;

R4, R7, and R8 are independently selected from the group consisting of H, —($C_1$-$C_4$) alkyl, and —($C_1$-$C_4$) substituted alkyl;

R5 is selected from the group consisting of H, —($C_1$-$C_6$) alkyl, and —$CH_2$R6;

R6 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH) (—O—($CH_2$)-phenyl), —O—P(=O)(—O—($CH_2$)-phenyl)$_2$, a carboxylic acid group, an amino carboxylic acid group, and a peptide;

R9 is selected from the group consisting of H, —($C_1$-$C_6$) alkyl, —($C_1$-$C_6$) substituted alkyl, —($C_3$-$C_9$)cycloalkyl, —($C_3$-$C_9$) substituted cycloalkyl, aryl, heteroaryl, and heterocyclyl;

Q is selected from the group consisting of aryl, heteroaryl, heterocyclyl, alkyl, substituted aryl, substituted heteroaryl, substituted heterocyclyl, and substituted alkyl;

T is —$CH_2$—, —C(O)—, or a bond; when T is a bond, Y is a bond, W is bond, X is —$CH_2$—, and m=1, n=1;

V and Z are independently selected from the group consisting of O, S, and H$_2$;

X is independently selected from the group consisting of —$CH_2$—, —NR8, S, O, and a bond;

Y and W are independently —$CH_2$—, or a bond;

m is 1 or 2;

n is 1 or 2;

wherein X, Y, and W cannot all be a bond.

The present invention also provides a pharmaceutical composition comprising a compound of formula Ia, Ib, IIa, or IIb as defined in claim 1 or a pharmaceutically acceptable salt thereof together with one or more pharmaceutically acceptable carriers or excipients. In an embodiment, the pharmaceutical composition further comprises a second chemotherapeutic agent.

The present invention further provides a method of treating a cell proliferative disorder, said method comprising administering to a subject in need thereof a therapeutically effective amount of a compound of formula Ia, Ib, IIa, or IIb as defined in claim 1, or a pharmaceutically acceptable salt thereof, or a prodrug or metabolite thereof, in combination with a pharmaceutically acceptable carrier, wherein said cell proliferative disorder is treated. In an embodiment, the cells with proliferative order contain DNA encoding c-Met. In a further embodiment, the cells have a constitutively enhanced c-Met activity.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE FIGURES

FIG. 1A sets forth the effect on HT29 cells of the inhibition of the c-Met pathway by met siRNA with and without ZvAD-FMK caspase inhibition.

FIG. 1B sets forth the effect of met siRNA on the knockdown of GAPDH and c-Met in HT29 cells.

DETAILED DESCRIPTION OF THE INVENTION

1

The present invention provides compounds of formula Ia, Ib, IIa, or IIb, or pharmaceutically acceptable salts thereof:

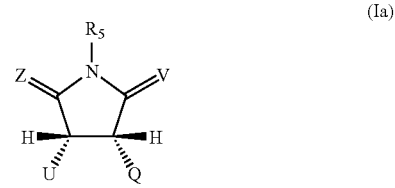

(Ia)

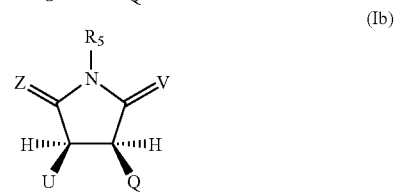

(Ib)

-continued

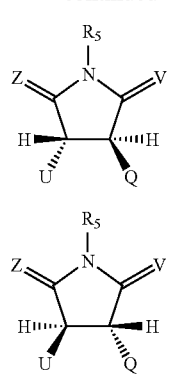
(IIa)

(IIb)

Where U is independently selected from:

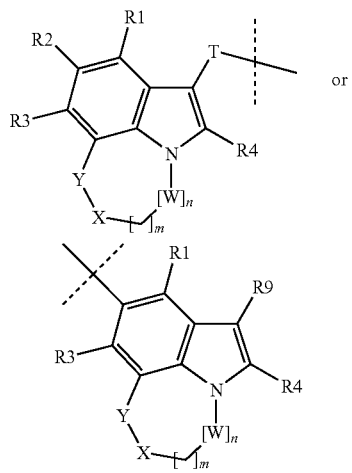

wherein:

R1, R2, and R3 are independently selected from the group consisting of H, F, Cl, Br, I, —NR7R8, —($C_1$-$C_6$)alkyl, —($C_1$-$C_6$) substituted alkyl, —($C_3$-$C_9$)cycloalkyl, —($C_3$-$C_9$) substituted cycloalkyl, —O—($C_1$-$C_6$) alkyl, —O—($C_3$-$C_9$) cycloalkyl, and —O—($C_3$-$C_9$) substituted cycloalkyl, aryl, heteroaryl, and heterocyclyl;

R4, R7, and R8 are independently selected from the group consisting of H, —($C_1$-$C_4$) alkyl, and —($C_1$-$C_4$) substituted alkyl;

R5 is selected from the group consisting of H, —($C_1$-$C_6$) alkyl, and $CH_2$R6;

R6 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH) (—O—($CH_2$)-phenyl), —O—P(=O)(—O—($CH_2$)-phenyl)$_2$, a carboxylic acid group, an amino carboxylic acid group, and a peptide;

R9 is selected from the group consisting of H, —($C_1$-$C_6$) alkyl, —($C_1$-$C_6$) substituted alkyl, —($C_3$-$C_9$)cycloalkyl, —($C_3$-$C_9$) substituted cycloalkyl, aryl, heteroaryl, and heterocyclyl;

Q is selected from the group consisting of aryl, heteroaryl, heterocyclyl, alkyl, substituted aryl, substituted heteroaryl, substituted heterocyclyl, and substituted alkyl;

T is —$CH_2$—, —C(O)—, or a bond; when T is a bond, Y is a bond, W is bond, X is —$CH_2$—, and m=1, n=1;

V and Z are independently selected from the group consisting of O, S, and $H_2$;

X is independently selected from the group consisting of —$CH_2$—, —NR8, S, O, and a bond;

Y and W are independently —$CH_2$—, or a bond;

m is 1 or 2;

n is 1 or 2;

wherein X, Y and W cannot all be a bond.

As used in this description and the accompanying claims, all technical and scientific terms used herein have the same meaning as commonly understood by one of ordinary skill in the art to which this invention belongs unless defined otherwise. In case of a conflict in terminology, the present specification controls. The following terms generally have the following meanings.

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Alkyl groups may be denoted by a range, thus, for example, a ($C_1$-$C_6$) alkyl group is an alkyl group having from one to six carbon atoms in the straight or branched alkyl backbone. Substituted and unsubstituted alkyl groups may independently be ($C_1$-$C_5$) alkyl, ($C_1$-$C_6$) alkyl, ($C_1$-$C_{10}$) alkyl. Unless expressly stated, the alkyl, ($C_3$-$C_{10}$) alkyl, or ($C_5$-$C_{10}$) alkyl. Unless expressly stated, the term "alkyl" does not include "cycloalkyl."

A "cycloalkyl" group refers to a cyclic alkyl group having the indicated number of carbon atoms in the "ring portion," where the "ring portion" may comprise one or more ring structures either as fused, spiro, or bridged ring structures. For example, a C3 to C6 cycloalkyl group (e.g., ($C_3$-$C_6$) cycloalkyl) is a ring structure having between 3 and 6 carbon atoms in the ring. When no range is given, then cycloalkyl has between three and nine carbon atoms (($C_3$-$C_9$) cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The terms "substituted alkyl" and "substituted cycloalkyl", refer to alkyl and cycloalkyl groups, as defined above, substituted with one or more substituents independently selected from the group consisting of fluorine, aryl, heteroaryl, —O—($C_1$-$C_6$) alkyl, and —NR7R8, where R7 and R8 are independently selected from the group consisting of hydrogen and —($C_1$-$C_6$) alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonaromatic carbocyclic or heterocyclic rings having from 4-9 members. Examples of fused aryl groups include benzocyclobutanyl, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of heteroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "substituted aryl" and "substituted heteroaryl" refer to aryl and heteroaryl groups, as defined above, substituted with one or more substituents independently selected from the group consisting of F, Cl, Br, I, —(C1-C6) alkyl, —(C1-C6)fluoro-substituted alkyl, —(C3-C9) cycloalkyl, —(C3-C9) fluoro-substituted cycloalkyl, —O—(C1-C6) alkyl, —O—(C1-C6) fluoro-substituted alkyl, —O—(C3-C9) cycloalkyl, and —O—(C3-C9) fluoro-substituted cycloalkyl, -aryl, —O-aryl, —O—(C1-C4) alkyl-aryl, —O—(C1-C4) alkyl-heterocycle, and —S(=O)$_2$—(C1-C6) alkyl.

The terms "heterocyclyl" or "heterocycle" refers to either saturated or unsaturated, stable non-aromatic ring structures that may be fused, spiro or bridged to form additional rings. Each heterocycle comprises one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

For the purposes of the R6 substituent, the term "carboxylic acid group" refers to a group of the form —O—C(=O)—(C$_1$-C$_6$) alkyl, —O—C(=O)—(C$_3$-C$_9$) cycloalkyl, —O—C(=O)-aryl, —O—C(=O)-heteroaryl, —O—(=O)-heterocycle, —O—C(=O)—(C$_1$-C$_6$) alkyl-aryl, —O—C(=O)—(C$_1$-C$_6$) alkyl-heteroaryl, or —O—C(=O)—(C$_1$-C$_6$) alkyl-heterocycle. Included in "carboxylic acid group" are groups of the form —O—C(=O)—(C$_1$-C$_6$) alkyl, —O—C(=O)—(C$_3$-C$_9$) cycloalkyl, —O—C(=O)-aryl, —O—C(=O)-heteroaryl, —O—C(=O)-heterocycle, —O—C(=O)—(C$_1$-C$_6$) alkyl-aryl, —O—C(=O)—(C$_1$-C$_6$) alkylheteroaryl, or —O—C(=O)—(C$_1$-C$_6$) alkyl-heterocycle substituted with one or more substituent independently selected from the group consisting of: F, Cl, Br, I, —OH, —SH, —NR5'R6', —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —S—(C$_1$-C$_6$) alkyl, —O—(C$_3$-C$_9$) cycloalkyl, —O—(C$_3$-C$_9$) substituted cycloalkyl, aryl, —O-aryl, —O—(C$_1$-C$_4$) alkyl-aryl, heteroaryl, heterocyclyl, —O—(C$_1$-C$_4$) alkyl-heterocycle, —(S(=O)$_2$)—(C$_1$-C$_6$) alkyl, —NH—C(=NH)—NH$_2$ (i.e., guanido), —COOH, and —C(=O)—NR5'R6', where R5' and R6' are independently selected from the group consisting of hydrogen, and —(C$_1$-C$_6$) alkyl. In addition, for the purposes of the R6 substituent the term "amino carboxylic acid group" refers to a carboxylic acid group, including carboxylic acid groups substituted with one or more of the above-stated substituents, which bears one or more independently selected amino groups of the form —NR5'R6' where R5' and R6' are independently selected from the group consisting of hydrogen and (C$_1$-C$_6$) alkyl.

In one embodiment of this invention, R6 is an alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof. In another embodiment the of the invention R6 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, L-valine.

For the purposes of the R6 substituent, the term "peptide" refers to a dipeptide, tripeptide, tetrapeptide or pentapeptide, which release two, three, four, or five amino or imino acids (e.g., proline) respectively upon hydrolysis. For the purpose of R6, peptides are linked to the remainder of the molecule through an ester linkage. In one embodiment, peptides of R6 are comprised of alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof; and in a more preferred version of this embodiment, the carboxyl group involved in the ester linkage is the carboxyl terminal COOH group of the peptide, as opposed to a side chain carboxyl. In another embodiment the of the invention R6 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; and in a more preferred version of this preferred embodiment, the carboxyl group involved in the ester linkage is the carboxyl terminal COOH group of the peptide, as opposed to a side chain carboxyl.

In an embodiment, Q is an indolyl group or an indolyl group substituted with one or more substituents independently selected from the group consisting of: F, Cl, Br, I, —(C$_1$-C$_6$) alkyl, —(C$_1$-C$_6$)fluoro-substituted alkyl, —(C$_3$-C$_9$) cycloalkyl, —(C$_3$-C$_9$) fluoro-substituted cycloalkyl, —O—(C$_1$-C$_6$) alkyl, —O—(C$_1$-C$_6$) fluoro-substituted alkyl, —O—(C$_3$-C$_9$) cycloalkyl, and —O—(C$_3$-C$_9$) fluoro-substituted cycloalkyl, -aryl, —O-aryl, —O—(C$_1$-C$_4$) alkyl-aryl, —O—(C$_1$-C$_4$) alkyl-heterocycle, and —S(=O)$_2$—(C$_1$-C$_6$) alkyl.

In an embodiment, both V and Z are O.

In an embodiment, R5 is H.

In an embodiment, X is selected from the group consisting of —(NR8)-, S, and O.

In an alternative embodiment, X is —CH$_2$—. In a further embodiment, Y is a bond. In an even further embodiment, m is 2, W is —CH$_2$—, and n is 1.

In an embodiment, U is

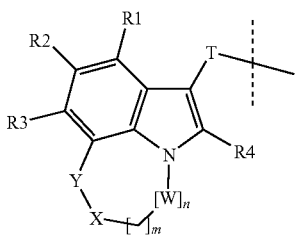

In an embodiment, T is —CH$_2$—. In an alternative embodiment, T is —C(O)—.

In a further embodiment, U is

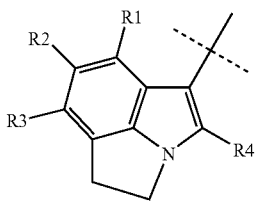

In an alternative embodiment, U is

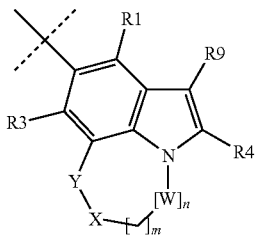

In an even further embodiment, the compound of the present invention is selected from the group consisting of (±)-trans-3-(5,6-dihydro-4H-pyrrolo[3,2,1-ij]quinolin-1-yl-methyl)-4-(1H-indol-3-yl)-pyrrolidine-2,5-dione, (±)-cis-3-(5,6-dihydro-4H-pyrrolo[3,2,1-ij]quinoline-1-carbonyl)-4-(1H-indol-3-yl)-pyrrolidine-2,5-dione, (±)-trans-3-(5,6-dihydro-4H-pyrrolo[3,2,1-ij]quinolin-8-yl)-4-(1H-indol-3-yl)-pyrrolidine-2,5-dione, (±)-trans-3-(5-bromo-1H-indol-3-yl)-4-(5,6-dihydro-4H-pyrrolo[3,2,1-ij]quinolin-8-yl)-pyrrolidine-2,5-dione, (±)-trans-3-(2-Chloro-phenyl)-4-(5,6-dihydro-4H-pyrrolo[3,2,1-ij]quinolin-8-yl)-pyrrolidine-2,5-dione, (±)-trans-3-(5,6-dihydro-4H-pyrrolo[3,2,1-ij]quinolin-8-yl)-4-(3-methoxy-phenyl)-pyrrolidine-2,5-dione, and (±)-trans-3-(4,5-dihydro-pyrrolo[3,2,1-hi]indol-1-yl)-4-(1H-indol-3-yl)-pyrrolidine-2,5-dione.

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na$^+$, K$^+$, Li$^+$, alkali earth metal salts such as Mg or Ca, or organic amine salts.

As used herein, the term "metabolite" means a product of metabolism of a compound of the present invention, or a pharmaceutically acceptable salt, analog or derivative thereof, that exhibits a similar activity in vivo to said compound of the present invention.

As used herein, the term "prodrug" means a compound of the present invention covalently linked to one or more pro-moieties, such as an amino acid moiety or other water solubilizing moiety. A compound of the present invention may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R5, may be selected based on solubility, stability, bioavailability, and/or in vivo delivery or uptake.

2. The Synthesis of Pyrrolidine-2,5-Diones

Standard synthetic methods and procedures for the preparation of organic molecules and functional group transformations and manipulations including the use of protective groups can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5th ed.; John Wiley & Sons: New York, 2001; and Greene, T. W.; Wuts, P. G. M. Protective Groups in Organic Synthesis, 3$^{rd}$ ed.; John Wiley & Sons: New York, 1999. The following descriptions of synthetic methods are designed to illustrate, but not limit, general procedures for the preparation of compounds of the invention.

2.1 General Procedures for the Synthesis of Pyrrolidine-2,5-Diones

The present invention provides for pyrrolidine-2,5-dione compounds of formula IAa, IBb, IIAa, or IIBb. The preparation of compounds of formulas IAa, IBb, IIAa, and IIBb may be achieved by a series of reactions commencing with the reaction of an oxoacetic acid ester of formula IV, VII, or XIII with an amide of formula III, VI or XI to form a pyrrole-2,5-dione of formula V, VIII, X, XII or XIV, followed by reduction to pyrrolidine-2,5-dione compounds of formula IAa, IBb, IIAa, or IIBb as shown in Schemes 1-5.

Scheme 1
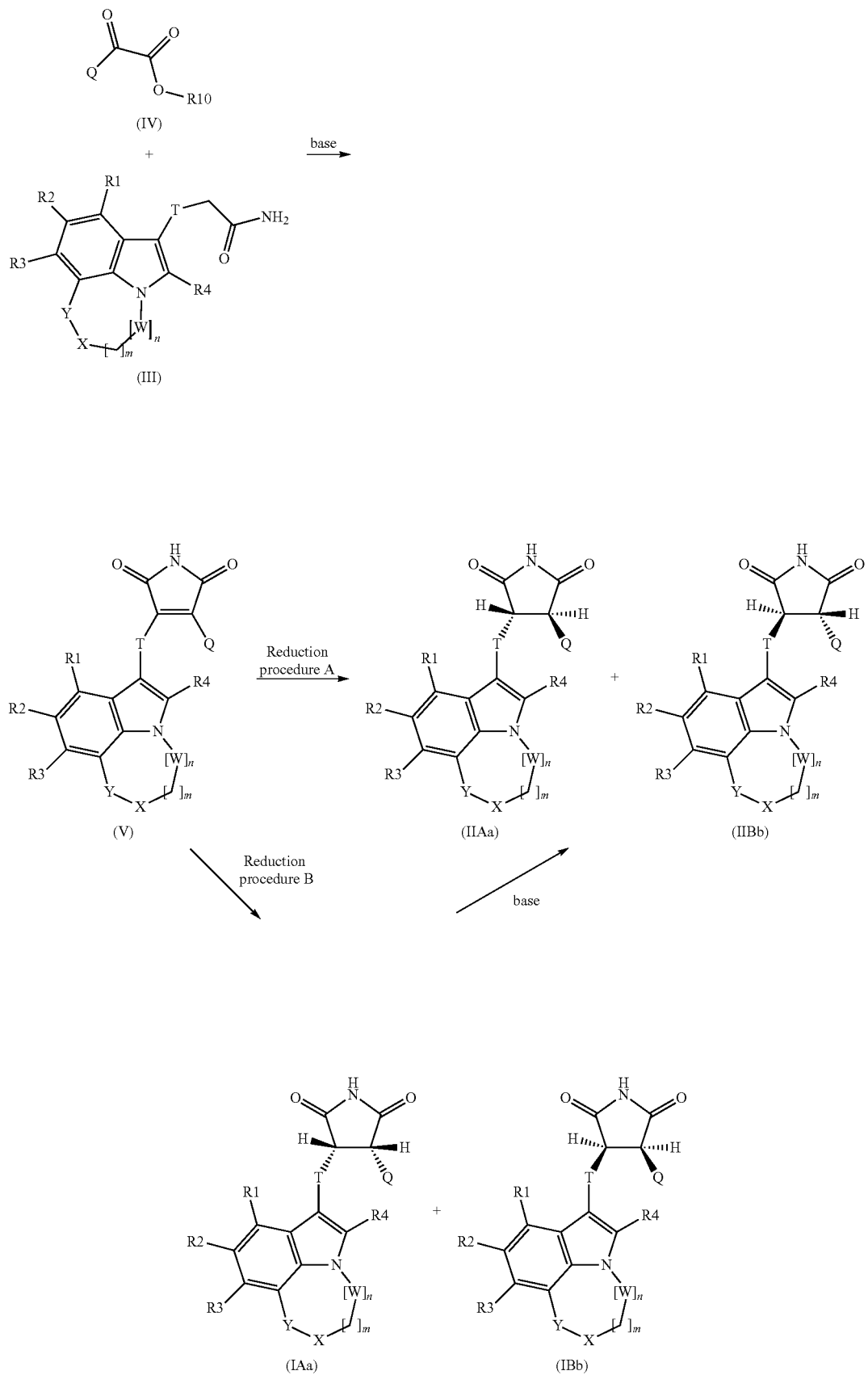

Scheme 2
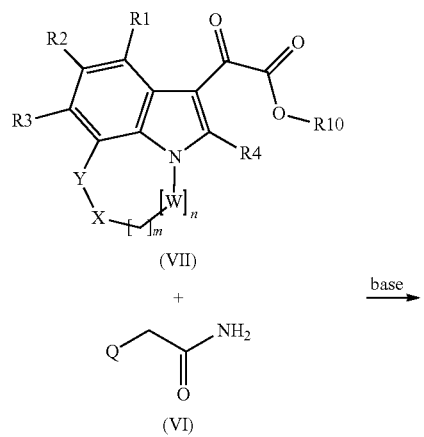
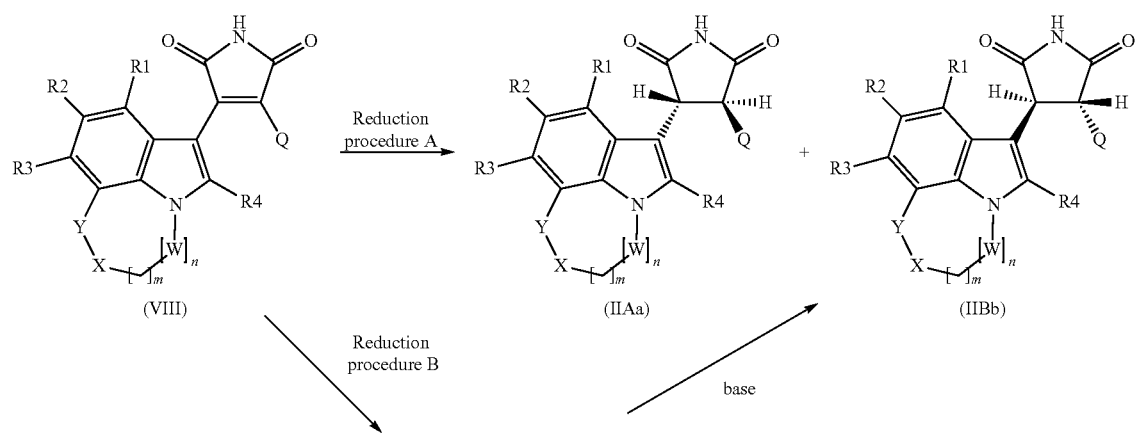
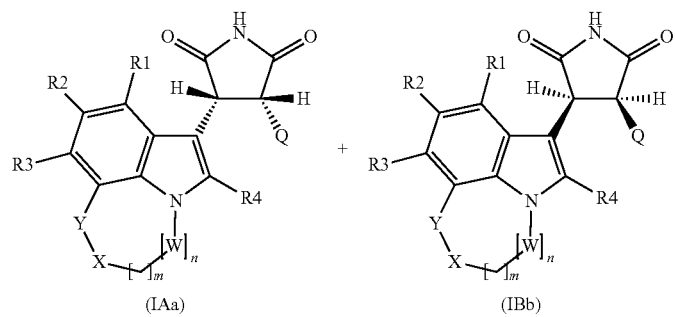

Scheme 3
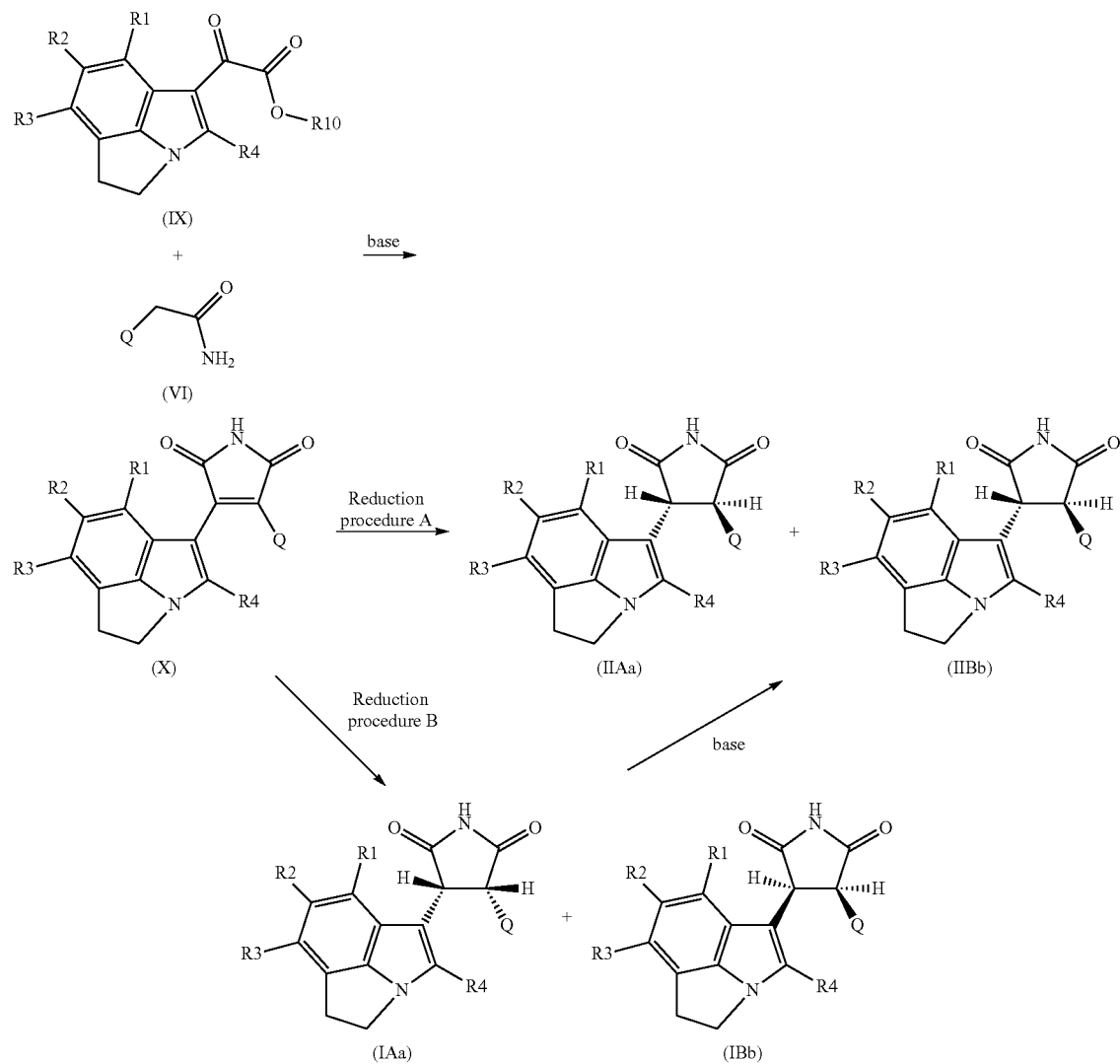
Scheme 4
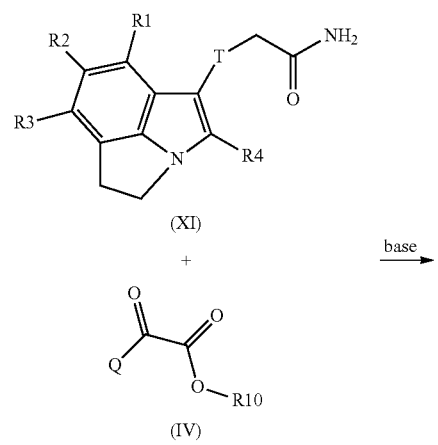

17
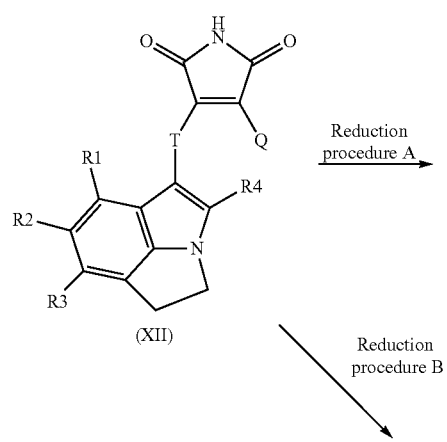
(XII)
-continued
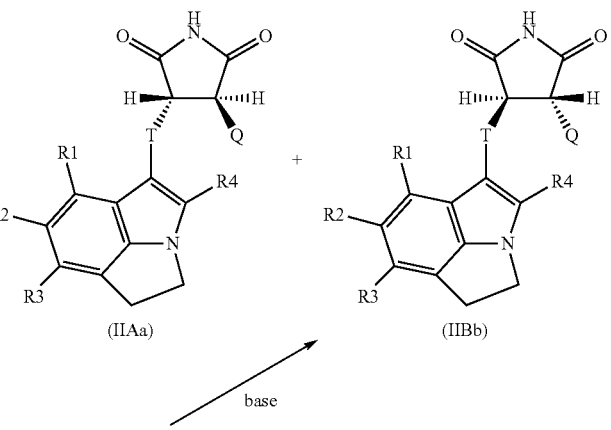
(IIAa)     (IIBb)
Reduction procedure A
Reduction procedure B
base
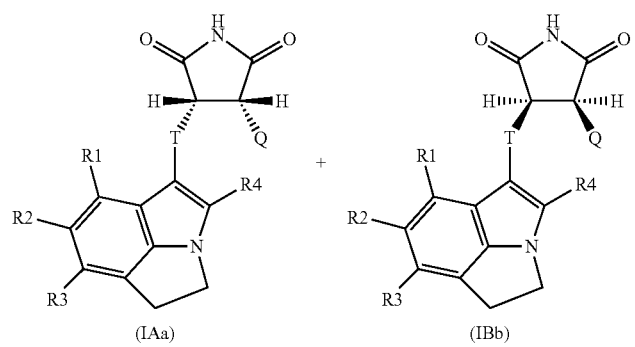
(IAa)     (IBb)
Scheme 5
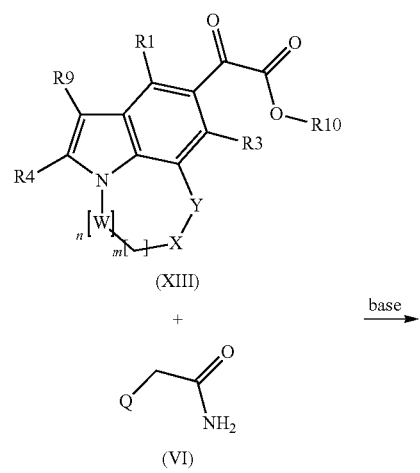
(XIII)
+
(VI)
base →

-continued

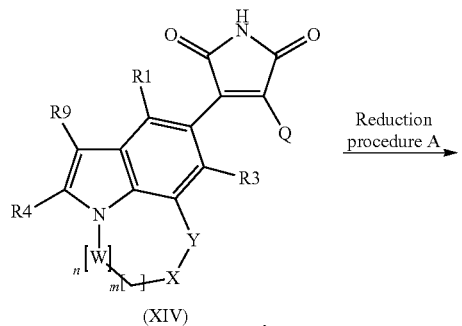
(XIV)

Reduction procedure A →

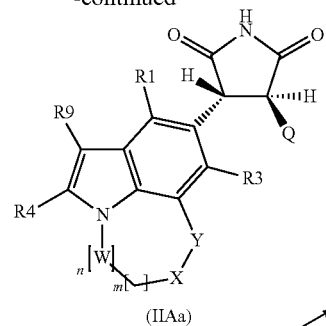
(IIAa)

+

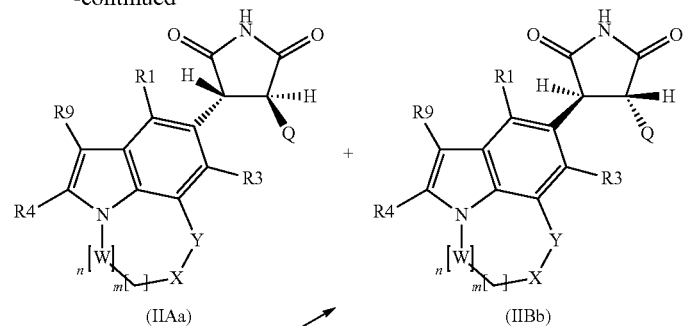
(IIBb)

Reduction procedure B ↓ base →

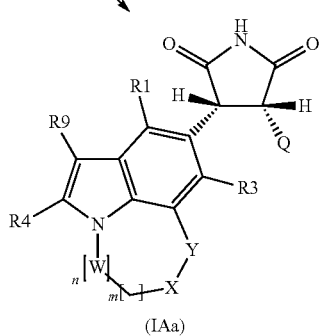
(IAa)

+

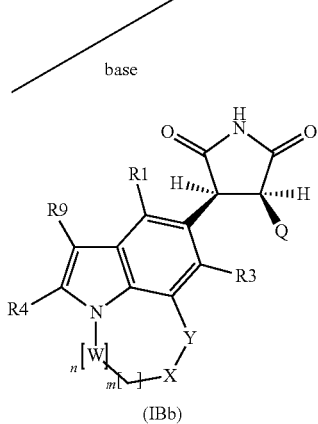
(IBb)

2.1.1. Synthesis of Pyrrole-2,5-Diones of Formula V, VIII, X, XII and XIV

The condensation of an oxoacetic acid ester of formula IV, VII, IX or XIII and a compound of formula III, VI or XI to produce compounds of formulas V, VIII, X, XII and XIV is conducted in any suitable anhydrous solvent including, but not limited to, tetrahydrofuran (THF), tetrahydropyran, diethyl ether and the like in the presence of base. For the purposes of the reaction, suitable oxoacetic acid esters of formula IV, VII, IX or XIII include, but are not limited to, alkyl esters where R10 is a (C1-C4) alkyl group, and preferred esters include the methyl and ethyl esters. Suitable bases for the reaction include alkaline metal salts of low molecular weight alkyl alcohols, including, but not limited to, alkaline metal salts of methanol, ethanol, propanol, isopropanol, n-butanol, isobutanol, and tent-butanol. Preferred alkaline metal salts of low molecular weight alkyl alcohols include sodium and potassium salts, with potassium tert-butoxide (t-BuOK) being the preferred base. Typically the reactions are conducted at 0° C. for 2 hours, however, both the time and temperature may be altered depending upon the specific substituents present on compounds of formula III, IV, VI, VII, IX, XI, and VIII, and the solvent employed. The reaction temperature may be varied from −78° C. to 37° C., and is preferably from −35° C. to 25° C., or more preferably from −15° C. to 10° C. Reaction times will generally vary inversely with the temperature employed, suitable times from about 15 minutes to 24 hours may be employed, more preferably, 30 minutes to 12 hours, and more preferably 1 to 6 hours.

2.1.2. Preparation of Compounds of Formulas IAa, IBb, IIAa and IIBb

Reduction of compounds of formulas V, VIII, X, XII and XIV to yield the corresponding pyrrolidine-2,5-diones having formulas IAa, IBb, IIAa, or IIBb may be conducted employing a variety of procedures including, but not limited to, reduction with catalytic hydrogenation (Procedure B), and reduction with magnesium in methanol (Procedure A). As indicated in Scheme 1, depending on the reduction reaction and conditions chosen, the reaction will yield principally compounds of formulas IAa and IBb, or principally compounds of formulas IIAa and IIBb.

Compounds of the formula IAa and IBb may be prepared by the direct reduction of compounds of the formula V, VIII, X, XII and XIV with catalytic hydrogenation. Catalytic hydrogenation of compounds of formulas V, VIII, X, XII and XIV may be conducted in a suitable solvent, such as tetrahydrofuran, ethyl acetate or alcohol over a noble metal catalyst under at least 1 atmosphere of hydrogen for 48 hours. A variety of low molecular weight alkyl alcohols may be employed to conduct the reduction, including n-propyl alcohol, isopropyl alcohol, ethanol or methanol. Preferably the alcohol is ethanol or methanol, and most preferably methanol. A noble metal catalyst (e.g., platinum, palladium, rhodium, ruthenium etc.) on charcoal is preferred for the reduction of compounds of formulas V, VIII, X, XII, and XIV. In more preferred embodiments, the noble metal catalyst is palladium on activated charcoal. While reduction compounds of formulas V, VIII, X, XII and XIV under 1 atmosphere of hydrogen at room temperature (25° C.) for 12-48 hours is generally suitable for preparation of pyrrolidine-2,5-diones, the pressure of hydrogen, reaction time, and the reaction temperature may be varied. Catalytic hydrogenation of 3-(5, 6-dihydro-4H-pyrrolo[3,2,1-ij]quinoline-1-carbonyl)-4-(1H-indol-3-yl)-pyrrole-2,5-dione is described in Example 6, Procedure B.

Pyrrole-2,5-diones of formula V, VIII, X, XII and XIV may be reduced to yield a mixture of compounds of formulas IIAa and IIBb by the reduction in anhydrous alcohol with a metal reducing agent. A preferred metal reducing agent is magnesium. The reaction is typically carried out under an inert atmosphere of nitrogen for 30 minutes to 6 hours by heating to reflux a compound of formula V, VIII, X, XII and XIV in an alcohol selected from the group consisting of methanol, ethanol, n-propanol, and isopropanol with magnesium turnings. Methanol is the preferred solvent for the reduction. In preferred embodiments the reaction is conducted for about 6 hours in methanol as described in Example 9, Procedure A, for the preparation of (±)-trans-3-(5,6-dihydro-4H-pyrrolo[3,2,1-ij]quinolin-1-ylmethyl)-4-(1H-indol-3-yl)-pyrrolidine-2,5-dione.

Compounds of IAa and/or IBb, which have the pyrrolidine ring substituents in the cis configuration, may be converted into a mixture of compounds of IIAa and IIBb, where the substituents are in the trans configuration, or into a mixture of all four isomers of formulas IAa, IBb, IIAa, and IIBb by treatment with base in a suitable solvent. A suitable solvent can be an alcohol, N,N-dimethylformamide or tetrahydrofuran. Typically the reaction employs an alkaline metal salt of a (C1-C4) alkyl alcohol in an alcohol solvent (e.g., sodium or potassium methoxide in methanol, sodium or potassium ethoxide in ethanol, sodium or potassium tert-butoxide in tert-butanol), with potassium tert-butoxide in tert-butanol as the preferred alkaline metal salt and solvent mixture. Reactions are generally conducted from 0° C. to the reflux temperature of the reaction mixture for 4 to 48 hours. In more preferred embodiments, the reactions are conducted from room temperature (25° C.) to the reflux temperature of the mixture for 8 to 24 hours, and in an even more preferred embodiment, the reaction is conducted at about 50° C. in a mixture of potassium tert-butoxide in tert-butanol for about 16 hours. Short reaction times and low temperatures favor formation of mixtures still containing compounds IAa and/or IBb.

2.1.3. Separation of Compounds of Formula IAa, IBb, IIAa, and IIBb

Where the isolation of an individual product having the structure of formulas IAa, IBb, IIAa, or IIBb is desired, the products may be separated by chromatography on one or more chromatography media. Chromatography may be carried out on a preparative scale or on an analytical scale to determine the identity and purity of the products present in a sample. Although any suitable chromatography media including, but not limited to, silica, C18 silica, reverse phase, ion exchange, chiral chromatographic media, or any combination thereof, may be advantageously employed for separations, the suitability of specific chromatographic media and conditions for the separation of products having formulas IAa, IBb, IIAa, and IIBb will depend upon the substituents present on the compounds. In preferred embodiments, chromatographic separations are conducted employing HPLC. In other preferred embodiments the separation is carried out using supercritical fluid chromatography. Where supercritical fluid chromatography is employed, $CO_2$, or mixtures of $CO_2$ with other solvents including acetonitrile (ACN), methanol, ethanol, isopropanol, or hexane, are the preferred mobile phase, with mixtures of $CO_2$ and methanol most preferred. A variety of chromatographic media (stationary phases) may be employed in supercritical fluid chromatography including, but not limited to: ChiralCel OA, OB, OD, or OJ; ChiralPak AD or AS; Cyclobond I, II, or III; and Chirobiotic T, V, and R media.

In another preferred embodiment, where the products are individual isomers of formulas IAa, IBb, IIAa, or IIBb, mixtures containing two or more of the isomeric forms may be separated by using CHIRALPAK® AD columns (Daicel (U.S.A.) Inc. Fort Lee, N.J.). In that embodiment, products are applied to the AD column in methanol and the column is subsequently eluted with methanol.

The individual racemic forms of compounds of formulas IAa, IBb, IIAa, or IIBb may also be resolved by physical methods, such as, for example, fractional crystallization or crystallization of diastereomeric derivatives. In addition, individual optical isomers can be obtained from racemic mixtures by conventional methods, such as, for example, salt formation with an optically active acid, where applicable, followed by crystallization.

2.2. Preparation of Compounds of Formula VI and VII where Y is a Bond

Compounds of formulas VI and VII, which are employed in the synthesis of pyrrole-2,5-dione of formulas V, VIII, X, XII and XIV, may be purchased or obtained via a variety of synthetic routes such as those set forth below.

2.2.1. Preparation of Compounds of Formula VII where Y is a Bond

Compounds of formula VII may be prepared from the corresponding compound of formula A, where X is selected from the group consisting of —($CH_2$)—, —(NR6)-, S and O, R8 is selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, and m is 1 or 2. Exemplary compounds of formula A include 1,2,3,4-tetra hydroquinoline, 1,2,3,4-tetrahydro-quinoxaline, 3,4-dihydro-2H-benzo[1,4]oxazine, 3,4-dihydro-2H-benzo[1,4]thiazine, 2,3,4,5-tetrahydro-1H-benzo[b]azepine, 2,3,4,5-tetrahydro-1H-benzo[b][1,4]diazepine, 6,7,8,9-tetrahydro-5-oxa-9-aza-benzocycloheptene, or 2,3,4,5-tetrahydro-benzo[b][1,4]thiazepine). The preparation begins with the conversion of a compound of formula A to the corresponding 3-substituted-2-oxopropionic acid ethyl ester of formula B. The ethyl ester of formula B is cyclized to form a compound of formula C, which is converted to the free acid D, which is decarboxylated to yield the desired tricyclic product E. Subsequent reaction of the tricyclic product E with oxalyl chloride and work-up in alcoholic base yields the corresponding compound of formula VII. Scheme 6 illustrates the reaction sequence beginning with compounds of formula A.

Some suitable conditions for the conversion of compounds of formula A into compounds of formula VII through the reaction sequence of Scheme 6 are described herein. Compounds of formula A may be converted to the corresponding 3-substituted-2-oxopropionic acid ethyl ester of formula B by treatment with bromoethyl pyruvate in an anhydrous ether, such as THF, at room temperature for about 24 hours. Treatment of the 3-substituted-2-oxopropionic acid ethyl ester of formula B with anhydrous $MgCl_2$ in 2-methoxyethanol at about 125° C. for 30 minutes to 2 hours, preferably for 1 hour, results in the formation of the corresponding tricyclic carboxylic acid ester of formula C. Subsequent conversion of this compound to the free acid of formula D may be accomplished by hydrolysis in aqueous base. In preferred embodiments the reaction is carried out in an aqueous base, including but not limited to NaOH or KOH, in the presence of alcohol as a co-solvent. Preferred alcohol co-solvents include methanol, ethanol, n-propanol, and isopropanol, with ethanol as a more preferred co-solvent. Reactions are typically conducted by heating the mixture to reflux for 2 hours, although the time and temperature of the reaction may be varied as needed. Oxidative decarboxylation of compounds of formula D may be conducted by a variety of procedures suitable for the decarboxylation of aromatic acids. In preferred embodiments the decarboxylation of compounds of formula D is conducted by heating the free acid with copper-chromite (CuO—Cr$_2$O$_3$) in quinoline for about 2 hours to yield the decarboxylated product of formula E. Conversion of compounds of formula E to compounds of formula VII may be accomplished by reaction with oxalyl chloride, followed by treatment with a mixture of an anhydrous alcohol and the alkaline metal salt of the alcohol, preferably sodium methoxide, or sodium ethoxide. The reaction of oxalyl chloride with compounds of formula E is typically conducted in anhydrous solvents including ethers at a temperature from about −78° C. to about 10° C. In preferred embodiments, the reaction is conducted at a temperature from about −25° C. to about 5° C. employing an ether as a solvent. In more preferred embodiments the reaction is conducted at 0° C. Preferred solvents for conducting the reaction include, but are not limited to tetrahydrofuran (THF), tetrahydropyran, diethyl ether and the like.

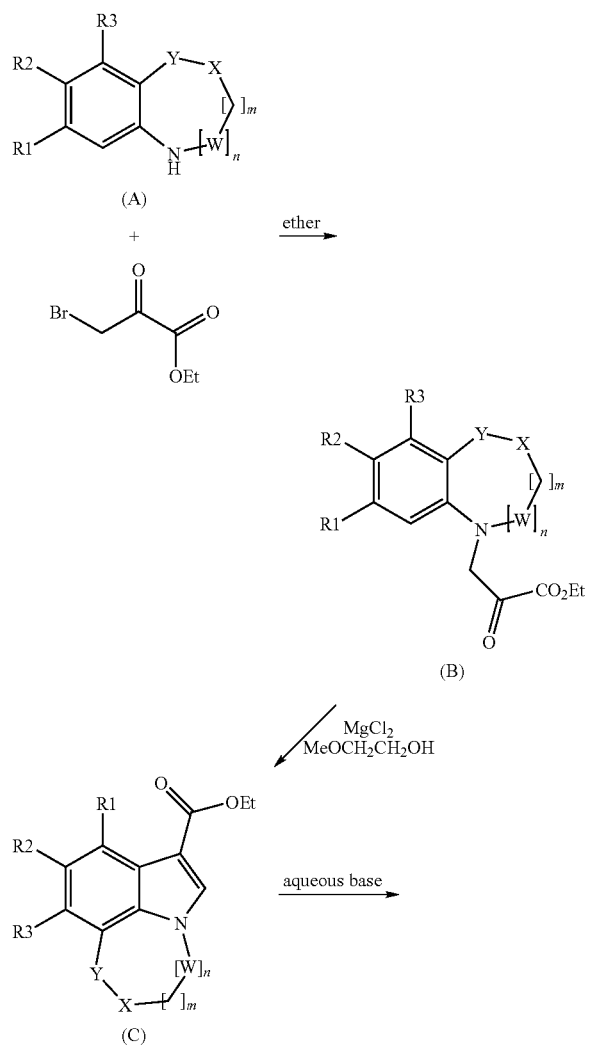

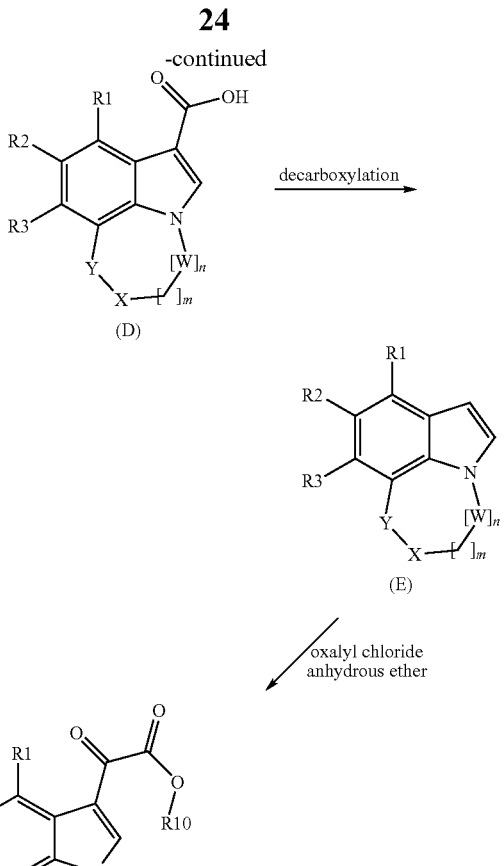

2.2.2. Preparation of Compounds of Formula VI

Compounds of formula VI, which are substituted acetamides, may be purchased or prepared from commercially available starting materials. Commercially available acetamides including: 2-(1H-indol-3-yl)-acetamide, 2-(5-methyl-1H-indol-3-yl)acetamide, 2-(5-methoxy-1H-indol-3-yl)acetamide, 2-(4-hydroxy-1H-indol-3-yl)acetamide, 2-phenylacetamide, 2-(4-methylphenyl)acetamide, 4-hydroxyphenylacetamide, 4-hydroxyphenylacetamide, N-cyclopentyl-2-(4-hydroxy-2-oxo-1,2-dihydro-3-quinolinyl)acetamide, 2-phenoxyacetamide, 2-(2-methylphenoxy)acetamide, 2-(4-fluorophenoxy)acetamide, 2-(4-pyridinyl)acetamide, and 2-[(4-chlorophenyl)sulfanyl]acetamide are available from a variety of sources including Sigma Aldrich Chemical Co., St. Louis Mo. A compound of formula VI may also be prepared from its corresponding free acid by conversion of the free acid to its acid chloride followed by reaction with ammonia.

3. Methods of Treatment

As used herein, a "subject" can be any mammal, e.g., a human, a primate, mouse, rat, dog, cat, cow, horse, pig, sheep, goat, camel. In a preferred aspect, the subject is a human. As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a non-cancerous condition, e.g., rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus. In another aspect, a cell proliferative disorder includes a precancer or a precancerous condition. In another aspect, a cell proliferative disorder includes cancer. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, chronic myelogenous leukemia, hematologic tumor, and lymphoid tumor, including metastatic lesions in other tissues or organs distant from the primary tumor site. Cancers to be treated include but are not limited to sarcoma, carcinoma, and adenocarcinoma. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers.

A "cell proliferative disorder of the hematologic system" is a cell proliferative disorder involving cells of the hematologic system. In one aspect, a cell proliferative disorder of the hematologic system includes lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. In another aspect, a cell proliferative disorder of the hematologic system includes hyperplasia, dysplasia, and metaplasia of cells of the hematologic system. In a preferred aspect, compositions of the present invention may be used to treat a cancer selected from the group consisting of a hematologic cancer of the present invention or a hematologic cell proliferative disorder of the present invention. In one aspect, a hematologic cancer of the present invention includes multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. In one aspect, cell proliferative disorders of the lung include all forms of cell proliferative disorders affecting lung cells. In one aspect, cell proliferative disorders of the lung include lung cancer, a precancer or precancerous condition of the lung, benign growths or lesions of the lung, and malignant growths or lesions of the lung, and metastatic lesions in tissue and organs in the body other than the lung. In a preferred aspect, compositions of the present invention may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchioalveolar carcinoma, giant cell carcinoma, spindle cell carcinoma, and large cell neuroendocrine carcinoma. In another aspect, lung cancer includes lung neoplasms having histologic and ultrastructural heterogeneity (e.g., mixed cell types).

In one aspect, cell proliferative disorders of the lung include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung. In another aspect, cell proliferative disorders of the lung include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In a preferred aspect, the cell proliferative disorder of the colon is colon cancer. In a preferred aspect, compositions of the present invention may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, cell proliferative disorders of the colon include all forms of cell proliferative disorders affecting colon cells. In one aspect, cell proliferative disorders of the colon include colon cancer, precancerous conditions of the colon, adenomatous polyps of the colon and metachronous lesions of the colon. In one aspect, a cell proliferative disorder of the colon includes adenoma. In one aspect, cell proliferative disorders of the colon are characterized by hyperplasia, metaplasia, and dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "cell proliferative disorder of the prostate" is a cell proliferative disorder involving cells of the prostate. In one aspect, cell proliferative disorders of the prostate include all forms of cell proliferative disorders affecting prostate cells. In one aspect, cell proliferative disorders of the prostate include prostate cancer, a precancer or precancerous condition of the prostate, benign growths or lesions of the prostate, and malignant growths or lesions of the prostate, and metastatic lesions in tissue and organs in the body other than the prostate. In another aspect, cell proliferative disorders of the prostate include hyperplasia, metaplasia, and dysplasia of the prostate.

A "cell proliferative disorder of the skin" is a cell proliferative disorder involving cells of the skin. In one aspect, cell proliferative disorders of the skin include all forms of cell proliferative disorders affecting skin cells. In one aspect, cell proliferative disorders of the skin include a precancer or precancerous condition of the skin, benign growths or lesions of the skin, melanoma, malignant melanoma and other malignant growths or lesions of the skin, and metastatic lesions in tissue and organs in the body other than the skin. In another aspect, cell proliferative disorders of the skin include hyperplasia, metaplasia, and dysplasia of the skin.

A "cell proliferative disorder of the ovary" is a cell proliferative disorder involving cells of the ovary. In one aspect, cell proliferative disorders of the ovary include all forms of cell proliferative disorders affecting cells of the ovary. In one aspect, cell proliferative disorders of the ovary include a precancer or precancerous condition of the ovary, benign growths or lesions of the ovary, ovarian cancer, malignant growths or lesions of the ovary, and metastatic lesions in tissue and organs in the body other than the ovary. In another aspect, cell proliferative disorders of the skin include hyperplasia, metaplasia, and dysplasia of cells of the ovary.

A "cell proliferative disorder of the breast" is a cell proliferative disorder involving cells of the breast. In one aspect, cell proliferative disorders of the breast include all forms of cell proliferative disorders affecting breast cells. In one aspect, cell proliferative disorders of the breast include breast cancer, a precancer or precancerous condition of the breast, benign growths or lesions of the breast, and malignant growths or lesions of the breast, and metastatic lesions in tissue and organs in the body other than the breast. In another aspect, cell proliferative disorders of the breast include hyperplasia, metaplasia, and dysplasia of the breast.

In one aspect, a cell proliferative disorder of the breast is a precancerous condition of the breast. In one aspect, compositions of the present invention may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

In a preferred aspect, the cell proliferative disorder of the breast is breast cancer. In a preferred aspect, compositions of the present invention may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructural heterogeneity (e.g., mixed cell types).

In a preferred aspect, a compound of the present invention may be used to treat breast cancer. In one aspect, a breast cancer that is to be treated includes familial breast cancer. In another aspect, a breast cancer that is to be treated includes sporadic breast cancer. In one aspect, a breast cancer that is to be treated has arisen in a male subject. In one aspect, a breast cancer that is to be treated has arisen in a female subject. In one aspect, a breast cancer that is to be treated has arisen in a premenopausal female subject or a postmenopausal female subject. In one aspect, a breast cancer that is to be treated has arisen in a subject equal to or older than 30 years old, or a subject younger than 30 years old. In one aspect, a breast cancer that is to be treated has arisen in a subject equal to or older than 50 years old, or a subject younger than 50 years old.

In one aspect, a breast cancer that is to be treated has arisen in a subject equal to or older than 70 years old, or a subject younger than 70 years old.

In one aspect, a breast cancer that is to be treated has been typed to identify a familial or spontaneous mutation in BRCA1, BRCA2, or p53. In one aspect, a breast cancer that is to be treated has been typed as having a HER2/neu gene amplification, as overexpressing HER2/neu, or as having a low, intermediate or high level of HER2/neu expression. In another aspect, a breast cancer that is to be treated has been typed for a marker selected from the group consisting of estrogen receptor (ER), progesterone receptor (PR), human epidermal growth factor receptor-2, Ki-67, CA15-3, CA 27-29, and c-Met. In one aspect, a breast cancer that is to be treated has been typed as ER-unknown, ER-rich or ER-poor. In another aspect, a breast cancer that is to be treated has been typed as ER-negative or ER-positive. ER-typing of a breast cancer may be performed by any reproducible means. In a preferred aspect, ER-typing of a breast cancer may be performed as set forth in Onkologie 27: 175-179 (2004). In one aspect, a breast cancer that is to be treated has been typed as PR-unknown, PR-rich or PR-poor. In another aspect, a breast cancer that is to be treated has been typed as PR-negative or PR-positive. In another aspect, a breast cancer that is to be treated has been typed as receptor positive or receptor negative. In one aspect, a breast cancer that is to be treated has been typed as being associated with elevated blood levels of CA 15-3, or CA 27-29, or both.

In one aspect, a breast cancer that is to be treated includes a localized tumor of the breast. In one aspect, a breast cancer that is to be treated includes a tumor of the breast that is associated with a negative sentinel lymph node (SLN) biopsy. In one aspect, a breast cancer that is to be treated includes a tumor of the breast that is associated with a positive sentinel lymph node (SLN) biopsy. In another aspect, a breast cancer that is to be treated includes a tumor of the breast that is associated with one or more positive axillary lymph nodes, where the axillary lymph nodes have been staged by any applicable method. In another aspect, a breast cancer that is to be treated includes a tumor of the breast that has been typed as having nodal negative status (e.g., node-negative) or nodal positive status (e.g., node-positive). In another aspect, a breast cancer that is to be treated includes a tumor of the breast that has metastasized to other locations in the body. In one aspect, a breast cancer that is to be treated is classified as having metastasized to a location selected from the group consisting of bone, lung, liver, or brain. In another aspect a breast cancer that is to be treated is classified according to a characteristic selected from the group consisting of metastatic, localized, regional, local-regional, locally advanced, distant, multicentric, bilateral, ipsilateral, contralateral, newly diagnosed, recurrent, and inoperable.

In one aspect, a compound of the present invention may be used to treat or prevent a cell proliferative disorder of the breast, or to treat or prevent breast cancer, in a subject having an increased risk of developing breast cancer relative to the population at large. In one aspect, a subject with an increased risk of developing breast cancer relative to the population at large is a female subject with a family history or personal history of breast cancer. In another aspect, a subject with an increased risk of developing breast cancer relative to the population at large is a female subject having a germ-line or spontaneous mutation in BRCA1 or BRCA2, or both. In one aspect, a subject with an increased risk of developing breast cancer relative to the population at large is a female subject with a family history of breast cancer and a germ-line or spontaneous mutation in BRCA1 or BRCA2, or both. In another aspect, a subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. In one aspect, a subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

In another aspect, a breast cancer that is to be treated has been histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. In another aspect, a breast cancer that is to be treated has been assigned a tumor grade according to the International Consensus Panel on the Treatment of Breast Cancer selected from the group consisting of grade 1, grade 1-2, grade 2, grade 2-3, or grade 3.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. For example, a normal cell possesses normally functioning cell cycle checkpoint control mechanisms, which prevent unregulated or abnormal growth.

As used herein, "contacting a cell" refers to a condition in which a compound or other composition of matter is in direct contact with a cell, or is close enough to induce a desired biological effect in a cell.

As used herein, "candidate compound" refers to a compound of the present invention that has been or will be tested in one or more in vitro or in vivo biological assays, in order to determine if that compound is likely to elicit a desired biological or medical response in a cell, tissue, system, animal or human that is being sought by a researcher or clinician. In one aspect, a candidate compound is a compound of formula Ia, Ib, IIa, or IIb. In a preferred aspect, the biological or medical response is treatment of cancer. In another aspect, the biological or medical response is treatment or prevention of a cell proliferative disorder. In one aspect, in vitro or in vivo biological assays include, but are not limited to, enzymatic activity assays, electrophoretic mobility shift assays, reporter gene assays, in vitro cell viability assays.

As used herein, "monotherapy" refers to administration of a single active or therapeutic compound to a subject in need thereof. Preferably, monotherapy will involve administration of a therapeutically effective amount of an active compound. For example, cancer monotherapy with IIa comprises administration of a therapeutically effective amount of IIa, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in the number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 60%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 60%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 60%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 60%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

As used herein, the term "selectively" means tending to occur at a higher frequency in one population than in another population. In one aspect, the compared populations are cell populations. In a preferred aspect, a compound of the present invention, or a pharmaceutically acceptable salt, prodrug, metabolite, analog or derivative thereof, acts selectively on a cancer or precancerous cell but not on a normal cell. In another preferred aspect, a compound of the present invention, or a pharmaceutically acceptable salt, prodrug, metabolite, analog or derivative thereof, acts selectively to modulate one molecular target (e.g., c-Met) but does not significantly modulate another molecular target (e.g., Protein Kinase C). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of the present invention or a pharmaceutically acceptable salt, prodrug, metabolite, analog or derivative thereof, modulates the activity of a molecular target (e.g., c-Met). In one aspect, modulating refers to stimulating or inhibiting an activity of a molecular target. Preferably, a compound of the present invention modulates the activity of a molecular target so as to stimulate or inhibit the activity of the molecular target by at least 2-fold relative to the activity of the molecular target under the same conditions but lacking only the presence of said compound. More preferably, a compound of the present invention may modulate the activity of a molecular target so as to stimulate or inhibit the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention demonstrates a minimum of a four fold differential, preferably a ten fold differential, more preferably a fifty fold differential, in the dosage required to achieve a biological effect. Preferably, a compound of the present invention demonstrates this differential across the range of inhibition, and the differential is exemplified at the $IC_{50}$, i.e., a 50% inhibition, for a molecular target of interest.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of c-Met. As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of ERK 1 or ERK 2, or both. As used herein, an activity of ERK 1 or ERK 2 refers to any biological function or activity that is carried out by ERK 1 or ERK 2. For example, a function of ERK 1 or ERK 2 includes phosphorylation of downstream target proteins.

In one aspect, activating refers to placing a composition of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is not a protein.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA.* 100(5): 2674-8. In an aspect, cell death occurs by apoptosis.

In a preferred aspect, an effective amount of a compound of the present invention, or a pharmaceutically acceptable salt, prodrug, metabolite, analog or derivative thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with a compound of the present invention, or a pharmaceutically acceptable salt, prodrug, metabolite, analog or derivative thereof, induces or activates cell death selectively in cancer cells. Preferably, administering to a subject in need thereof a compound of the present invention, or a pharmaceutically acceptable salt, prodrug, metabolite, analog or derivative thereof, induces or activates cell death selectively in cancer cells. In another aspect, contacting a cell with a compound of the present invention, or a pharmaceutically acceptable salt, prodrug, metabolite, analog or derivative thereof, induces cell death selectively in one or more cells affected by a cell proliferative disorder. Preferably, administering to a subject in need thereof a compound of the present invention, or a pharmaceutically acceptable salt, prodrug, metabolite, analog or derivative thereof, induces cell death selectively in one or more cells affected by a cell proliferative disorder.

In a preferred aspect, the present invention relates to a method of treating or preventing cancer by administering a compound of the present invention, or a pharmaceutically acceptable salt, prodrug, metabolite, analog or derivative thereof to a subject in need thereof, where administration of the compound of the present invention, or a pharmaceutically acceptable salt, prodrug, metabolite, analog or derivative thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

In additional aspects, a compound of the present invention, or a pharmaceutically acceptable salt, prodrug, metabolite, analog or derivative thereof, may be administered in combination with a second chemotherapeutic agent. The second chemotherapeutic agent may be, without limitation, a taxane, an aromatase inhibitor, an anthracycline, a microtubule targeting drug, a topoisomerase poison drug, a targeted monoclonal or polyclonal antibody, an inhibitor of a molecular target or enzyme (e.g., a kinase inhibitor), or a cytidine analogue drug. In preferred aspects, the chemotherapeutic agent can be, but not restricted to, tamoxifen, raloxifene, anastrozole, exemestane, letrozole, HERCEPTIN® (trastuzumab), GLEEVEC® (imatanib), TAXOL® (paclitaxel), cyclophosphamide, lovastatin, minosine, araC, 5-fluorouracil (5-FU), methotrexate (MTX), TAXOTERE® (docetaxel), ZOLADEX® (goserelin), vincristin, vinblastin, nocodazole, teniposide, etoposide, GEMZAR® (gemcitabine), epothilone, navelbine, camptothecin, daunonibicin, dactinomycin, mitoxantrone, amsacrine, doxorubicin (adriamycin), epirubicin or idarubicin or agents listed in www.cancer.org/docroot/cdg/cdg_0.asp. In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

A compound of the present invention, or a pharmaceutically acceptable salt, prodrug, metabolite, analog or derivative thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin. Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, a compound of the present invention, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of the present invention, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The definitions in this description apply to the description and the accompanying claims, unless the context otherwise requires.

4. The Pharmaceutical Compositions and Formulations

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

All patents, patent applications and references cited herein are incorporated by reference herein in their entirety.

EXAMPLES

Examples are provided below to further illustrate different features of the present invention. The examples also illustrate useful methodology for practicing the invention. These examples do not limit the claimed invention.

Example 1

Preparation of 3-(5,6-dihydro-4H-pyrrolo[3,2,1-ij] quinolin-1-yl)-3-oxo-propionitrile

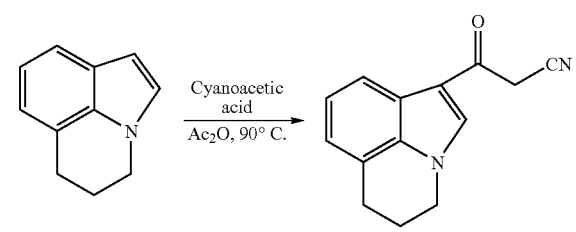 [SMILES: c1cc2c3c(c1)ccn3CCC2 ; N#CCC(=O)c1cn2c3c(cccc13)CCC2]

5,6-dihydro-4H-pyrrolo[3,2,1-ij]quinoline (3.0 g, 19.1 mmol) and cyanoacetic acid (1.7 g, 20.0 mmol) in acetic anhydride (50 ml) were heated to 90° C. for 1.5 hours. After cooling to room temperature the product precipitated out, was filtered off, washed with cold methanol and dried under reduced pressure to obtain 3-(5,6-dihydro-4H-pyrrolo[3,2,1-ij]quinolin-1-yl)-3-oxo-propionitrile as cream colored crystals (3.457 g). 400 MHz $^1$H NMR (CDCl$_3$) δ: 7.99 (d, J=7.6 Hz 1H), 7.83 (s, 1H), 7.25 (s, 1H), 7.07 (d, J=6.4 Hz, 1H), 4.23 (m, 2H), 3.88 (s, 2H), 3.01 (m, 2H), 2.28 (m, 2H); LCMS: 225 [M+H]

Example 2

Preparation of (E)-3-(5,6-dihydro-4H-pyrrolo[3,2,1-ij]quinolin-1-yl)-acrylonitrile

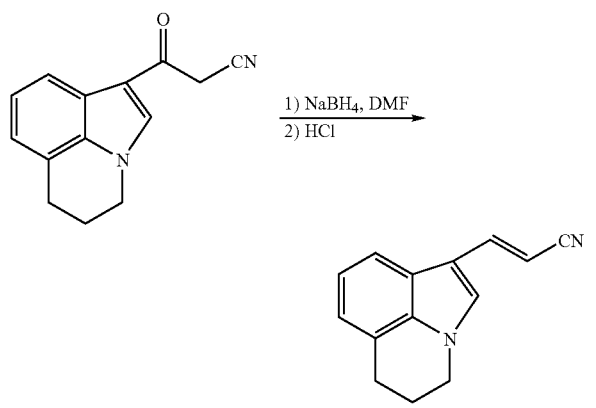

To a room temperature stirred solution of 3-(5,6-dihydro-4H-pyrrolo[3,2,1-ij]quinolin-1-yl)-3-oxo-propionitrile (1.0 g, 4.5 mmol) in anhydrous N,N-dimethylformamide (20 ml) was added excess sodium borohydride in small portions over 3 days. After 5 days the mixture was quenched with 1M hydrochloric acid (50 ml) and extracted with ethyl acetate (3×100 ml). The organic layer was dried over anhydrous magnesium sulfate and evaporated to dryness. The residue obtained was purified by flash column chromatography (SiO$_2$, 20% EtOAc in hexanes) to afford (E)-3-(5,6-dihydro-4H-pyrrolo[3,2,1-ij]quinolin-1-yl)-acrylonitrile as an off white solid (348 mg). 400 MHz $^1$H NMR (CDCl$_3$) δ: 7.55 (d, J=8.0 Hz, 1H), 7.5 (d, J=16.4 Hz, 1H), 7.3 (s, 1H), 7.18 (t, J=7.6 Hz, 1H), 7.03 (dd, J=0.8 and 6.8 Hz, 1H), 5.7 (d, J=16.4 Hz, 1H), 4.17 (t, J=5.6 Hz, 2H), 3.0 (t, J=6.4 Hz, 2H), 2.28-2.22 (m, 2H); LCMS: 208 [M+].

Example 3

Preparation of 3-(5,6-dihydro-4H-pyrrolo[3,2,1-ij]quinolin-1-yl)-propionitrile

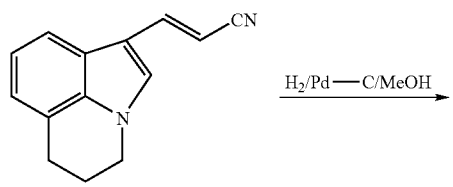

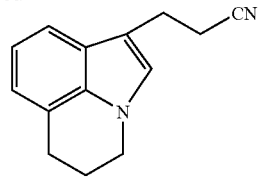

(E)-3-(5,6-dihydro-4H-pyrrolo[3,2,1-ij]quinolin-1-yl)-acrylonitrile (348 mg, 1.7 mmol) and 10% Pd—C (50 mg) in methanol (20 ml) were stirred at room temperature under 1 atmosphere of hydrogen gas for 6 hours. The mixture was filtered through celite washed with methanol and evaporated to dryness to yield 3-(5,6-dihydro-4H-pyrrolo[3,2,1-ij]quinolin-1-yl)-propionitrile as an off white solid (310 mg). 400 MHz $^1$H NMR (CDCl$_3$) δ: 7.32 (d, J=8.4 Hz, 1H), 7.03-6.96 (m, 2H), 6.91 (d, J=6.8 Hz, 1H), 4.11 (t, J=5.6 Hz, 2H), 3.11 (t, J=6.8 Hz, 2H), 2.97 (t, J=6.4 Hz, 2H), 2.66 (t, J=7.2 Hz, 2H), 2.26-2.19 (m, 2H); LCMS: 211 [M+H].

Example 4

Preparation of 3-(5,6-dihydro-4H-pyrrolo[3,2,1-ij]quinolin-1-yl)-propionamide

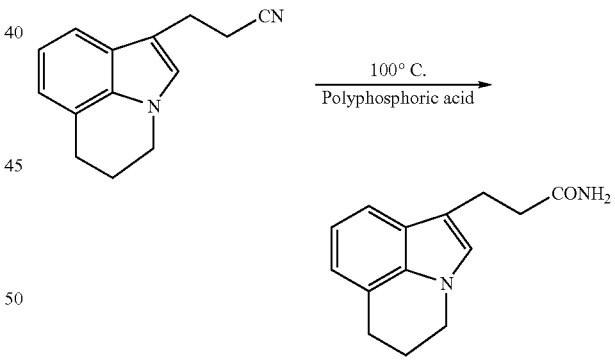

3-(5,6-dihydro-4H-pyrrolo[3,2,1-ij]quinolin-1-yl)-propionitrile (300 mg, 1.4 mmol) in polyphosphoric acid (8 ml) was heated to 100° C. for 3 hours. The mixture was then added to water (150 ml) and triturated to give a precipitate. The precipitate was filtered off, washed with water and dried under reduced pressure to give 3-(5,6-dihydro-4H-pyrrolo[3,2,1-ij]quinolin-1-yl)-propionamide as a tan powder (249 mg). 400 MHz $^1$H NMR (DMSO-d$_6$) δ: 7.31 (s, 2H), 7.06 (s, 1H), 6.9-6.7 (m, 3H), 4.08 (s, 2H), 2.89 (s, 4H), 2.4 (m, 2H), 2.1 (m, 2H); LCMS: 229 [M+H].

Example 5

Preparation of 3-(5,6-dihydro-4H-pyrrolo[3,2,1-ij]quinolin-1-ylmethyl)-4-(1H-indol-3-yl)-pyrrole-2,5-dione

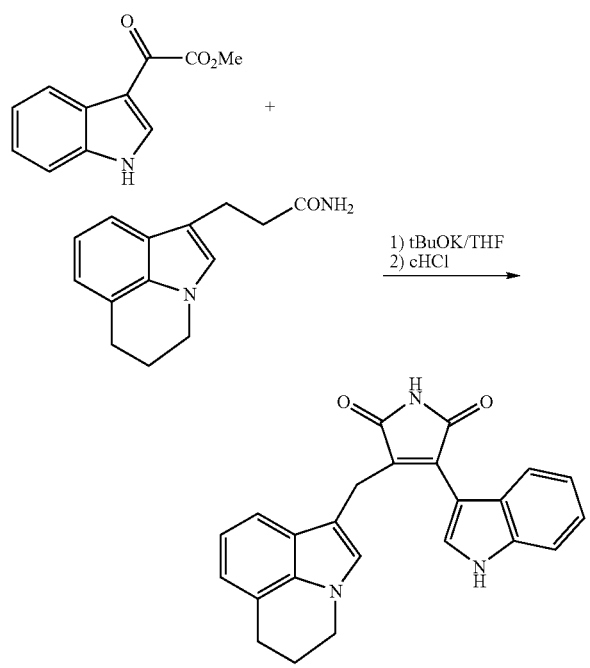

To a solution of 3-(5,6-dihydro-4H-pyrrolo[3,2,1-ij]quinolin-1-yl)-propionamide (249 mg, 1.1 mmol) and (1H-indol-3-yl)-oxo-acetic acid methyl ester (244 mg, 1.2 mmol) in anhydrous tetrahydrofuran (10 ml) at 0° C. was added potassium tert-butoxide (4.36 ml, 4.36 mmol; 1M in tetrahydrofuran). The mixture was allowed to warm to room temperature for 2 hours. Concentrated hydrochloric acid (4 ml) was added and the mixture stirred at room temperature for a further 30 minutes. The mixture was poured into ethyl acetate (250 ml), washed with water (750 ml) and purified by flash column chromatography (SiO$_2$, 30 to 40% EtOAc in hexanes) to afford 3-(5,6-dihydro-4H-pyrrolo[3,2,1-ij]quinolin-1-ylmethyl)-4-(1H-indol-3-yl)-pyrrole-2,5-dione as an orange foam (226 mg). 400 MHz $^1$H NMR (CDCl$_3$) δ: 8.54 (s, 1H), 7.80 (d, J=8.4 Hz, 1H), 7.53 (d, J=3.2 Hz, 1H), 7.42 (m, 1H), 7.3-7.25 (m, 1H), 7.21-7.17 (m, 1H), 7.09 (dd, J=1.6 and 7.2 Hz, 1H), 6.92-6.86 (m, 2H), 4.15-4.04 (m, 4H), 2.95 (t, J=6.4 Hz, 2H), 2.22-2.16 (m, 2H); LCMS: 382 [M+H].

Example 6

Procedure A: Reduction of 3-(5,6-dihydro-4H-pyrrolo[3,2,1-ij]quinolin-1-ylmethyl)-4-(1H-indol-3-yl)-pyrrole-2,5-dione by Magnesium in Methanol

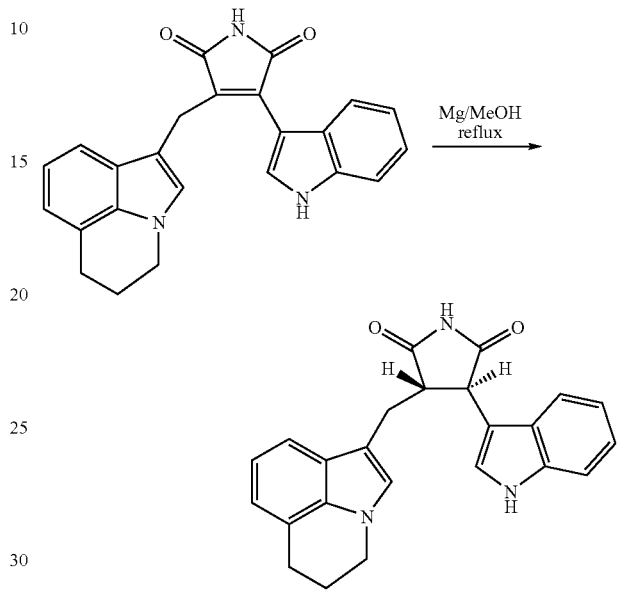

To a solution of 3-(5,6-dihydro-4H-pyrrolo[3,2,1-ij]quinolin-1-ylmethyl)-4-(1H-indol-3-yl)-pyrrole-2,5-dione (207 mg, 0.54 mmol) in anhydrous methanol (12 ml) was added magnesium turnings (264 mg, 10.7 mmol). The mixture was heated to reflux for 1.5 hours. The mixture was separated between ethyl acetate (200 ml) and water (600 ml), the organic layer dried over anhydrous magnesium sulfate and evaporated to dryness to give a pale yellow brown solid. The solid was triturated with methanol and the solids filtered off and washed with ice cold methanol to yield (±)-trans-3-(5,6-dihydro-4H-pyrrolo[3,2,1-ij]quinolin-1-ylmethyl)-4-(1H-indol-3-yl)-pyrrolidine-2,5-dione as an off white powder (83 mg). M.p.=215-218° C.; 400 MHz $^1$H NMR (DMSO-d$_6$) δ: 11.28 (s, 1H), 11.00 (s, 1H), 7.35-6.75 (m, 9H), 4.07 (m, 2H), 3.98 (d, J=5.2 Hz, 1H), 3.26-3.16 (m, 3H), 2.89 (m, 2H), 2.09 (m, 2H); LCMS: 384 [M+H].

Example 7

Preparation of 3-(5,6-dihydro-4H-pyrrolo[3,2,1-ij]quinolin-1-yl)-3-oxo-propionamide

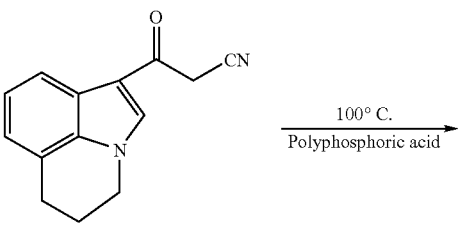

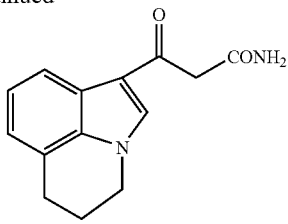

3-(5,6-dihydro-4H-pyrrolo[3,2,1-ij]quinolin-1-yl)-3-oxo-propionitrile (2.71 g, 12.1 mmol) in polyphosphoric acid (25 ml) was heated to 100° C. for 3 hours. The mixture was then added to ice water (250 ml) and triturated to give a precipitate. The precipitate was filtered off washed with water and dried under reduced pressure to give 3-(5,6-dihydro-4H-pyrrolo[3,2,1-ij]quinolin-1-yl)-3-oxo-propionamide as a brown powder (2.65 g). M.p.=200-201° C.; 400 MHz $^1$H NMR (DMSO-$d_6$) δ: 8.3 (s, 1H), 7.88 (d, J=7.6 Hz, 1H), 7.52 (s, 1H), 7.14-6.99 (m, 3H), 4.24 (t, J=5.6 Hz, 2H), 3.65 (s, 2H), 2.94 (t, J=6.0 Hz, 2H), 2.18-2.11 (m, 2H); LCMS: 243 [M+H].

Example 8

Preparation of 3-(5,6-dihydro-4H-pyrrolo[3,2,1-ij]quinoline-1-carbonyl)-4-(1H-indol-3-yl)-pyrrole-2,5-dione

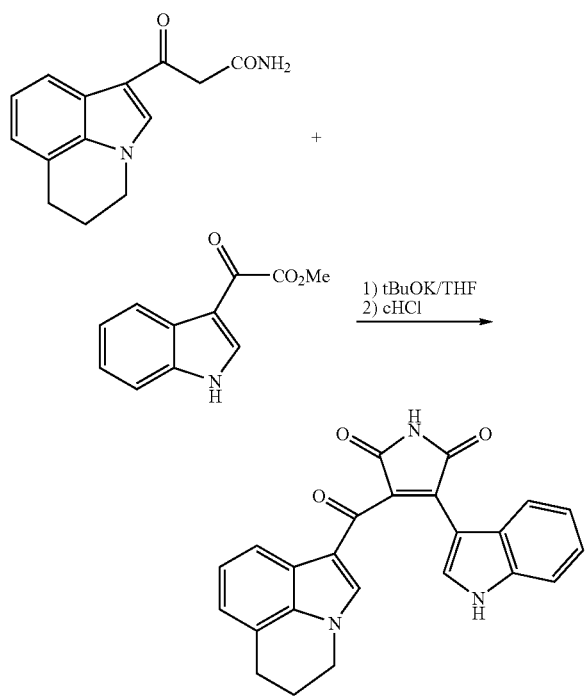

To a solution of 3-(5,6-dihydro-4H-pyrrolo[3,2,1-ij]quinolin-1-yl)-3-oxo-propionamide (2.0 g, 8.3 mmol) and (1H-indol-3-yl)-oxo-acetic acid methyl ester (1.8 g, 8.8 mmol) in anhydrous tetrahydrofuran (40 ml) at room temperature was added potassium tert-butoxide (26 ml, 26.0 mmol; 1M solution in tetrahydrofuran). After 45 minutes concentrated hydrochloric acid (10 ml) was added. Water (500 ml) was added to the mixture which was then extracted with ethyl acetate (350 ml). The organic layer was dried over anhydrous magnesium sulfate and evaporated to dryness. The residue obtained was sonicated with ethyl acetate (50 ml) to afford 3-(5,6-dihydro-4H-pyrrolo[3,2,1-ij]quinoline-1-carbonyl)-4-(1H-indol-3-yl)-pyrrole-2,5-dione as an orange solid (2.58 g). M.p.=>300° C.; 400 MHz $^1$H NMR (DMSO-$d_6$) δ: 11.99 (s, 1H), 11.12 (s, 1H), 8.18 (s, 1H), 8.13 (s, 1H), 7.93 (m, 1H), 7.52 (d, J=8.0 Hz, 1H), 7.40 (d, J=8.4 Hz, 1H), 7.18 (m, 1H), 7.06-7.01 (m, 2H), 6.85 (m, 1H), 4.11 (m, 2H), 2.90 (m, 2H), 2.08 (m, 2H); LCMS: 396 [M+H].

Example 9

Procedure B: Reduction of 3-(5,6-dihydro-4H-pyrrolo[3,2,1-ij]quinoline-1-carbonyl)-4-(1H-indol-3-yl)-pyrrole-2,5-dione with Hydrogen in the Presence of Palladium on Carbon

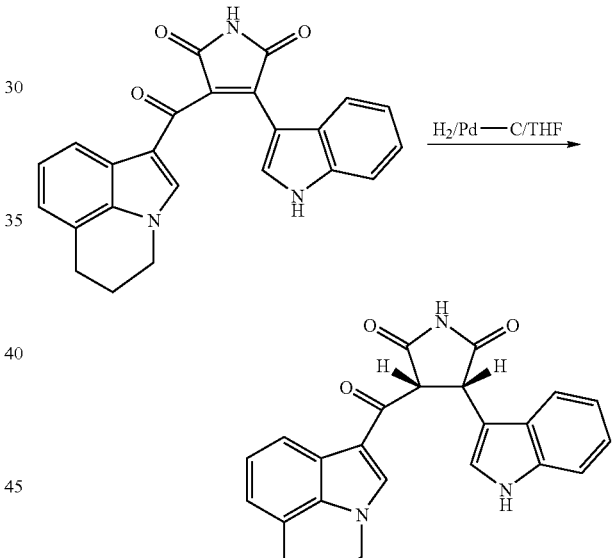

3-(5,6-dihydro-4H-pyrrolo[3,2,1-ij]quinoline-1-carbonyl)-4-(1H-indol-3-yl)-pyrrole-2,5-dione (500 mg, 1.26 mmol) and 10% Pd—C (300 mg) in anhydrous tetrahydrofuran (60 ml) was stirred at room temperature under 1 atmosphere of hydrogen gas for 1 day. The mixture was filtered through celite and evaporated to dryness. The residue obtained was purified by flash column chromatography (SiO$_2$, 65% EtOAc in hexanes) to yield (±)-cis-3-(5,6-dihydro-4H-pyrrolo[3,2,1-ij]quinoline-1-carbonyl)-4-(1H-indol-3-yl)-pyrrolidine-2,5-dione as a pale yellow powder (186 mg). M.p.=283-285° C.; 400 MHz $^1$H NMR (DMSO-$d_6$) δ: 11.64 (s, 1H), 11.1 (s, 1H), 8.46 (s, 1H), 7.92 (d, J=8.0 Hz, 1H), 7.42-7.36 (m, 3H), 7.19-6.97 (m, 4H), 4.85 (dd, J=5.0 and 46 Hz, 2H), 4.27-4.15 (m, 2H), 2.98-2.88 (m, 2H), 2.18-2.08 (m, 2H); LCMS: 398 [M+H].

Example 10

Preparation of 1,2,5,6-tetrahydro-4H-pyrrolo[3,2,1-ij]quinoline

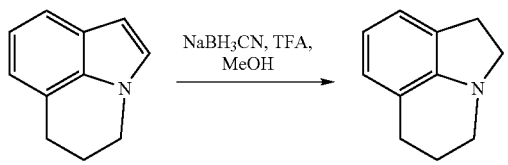 [SMILES: c1cc2c3c(c1)ccn3CCC2 ; c1cc2c3c(c1)CCN3CCC2]

A solution of 5,6-dihydro-4H-pyrrolo[3,2,1-ij]quinoline (4.0 g, 25.5 mmol) in methanol (100 ml) was treated with sodium cyanoborohydride (1.5 g, 23.9 mmol) then cooled to 0° C. Trifluoroacetic anhydride (15 ml) was added dropwise over 15 minutes, then the reaction was allowed to warm to room temperature and stirred for a further 2 hours. The reaction was basified with 5M aqueous potassium hydroxide then diluted with water (500 ml). The mixture was extracted with dichloromethane (3×100 ml) and the combined organic extracts were dried with anhydrous sodium sulfate and evaporated to dryness to obtain 1,2,5,6-tetrahydro-4H-pyrrolo[3,2,1-ij]quinoline as a colorless oil (4.0 g) which was used without further purification. LCMS: 160 [M+H].

Example 11

Preparation of 8-bromo-1,2,5,6-tetrahydro-4H-pyrrolo[3,2,1-ij]quinoline

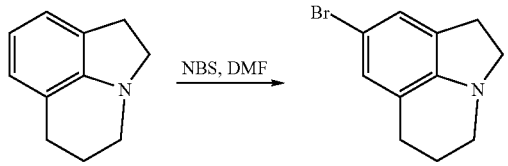 [SMILES: c1cc2c3c(c1)CCN3CCC2 ; Brc1cc2c3c(c1)CCN3CCC2]

A solution of 1,2,5,6-tetrahydro-4H-pyrrolo[3,2,1-ij]quinoline (4.0 g, 25.2 mmol) in N,N-dimethylformamide (160 ml) cooled to −30° C. was treated with a solution of N-bromosuccinimide (4.5 g, 25.3 mmol) in N,N-dimethylformamide (30 ml) dropwise over 5 minutes. The mixture was stirred for a further 15 minutes then treated with 10% aqueous sodium sulfite (100 ml) then diluted with water (500 ml) and ethyl acetate (300 ml). The aqueous layer was removed and the organic layer was washed with saturated aqueous sodium bicarbonate (100 ml), then water (3×150 ml). The organic layer was dried with anhydrous sodium sulfate and evaporated to dryness to give 8-bromo-1,2,5,6-tetrahydro-4H-pyrrolo[3,2,1-ij]quinoline as a pale brown oil (5.2 g) which was used without further purification. 400 MHz $^1$H NMR (CDCl$_3$) δ: 7.02 (m, 1H), 6.94 (m, 1H), 3.25 (t, 2H), 2.95 (m, 2H), 2.89 (t, 2H), 2.65 (t, 2H), 2.06 (m, 2H); LCMS: 238 and 240 [M+H].

Example 12

Preparation of oxo-(1,2,5,6-tetrahydro-4H-pyrrolo[3,2,1-ij]quinolin-8-yl)-acetic acid methyl ester

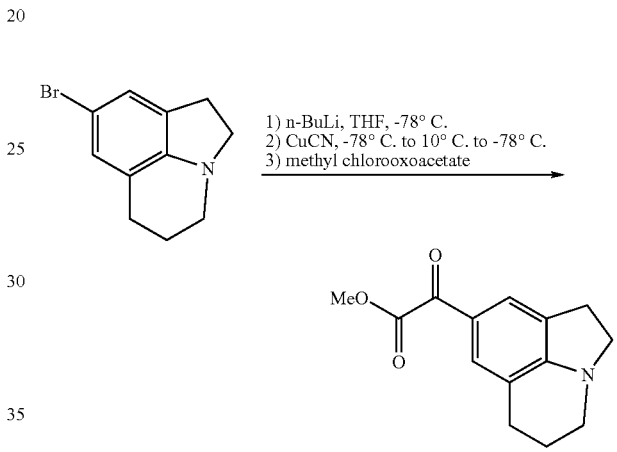

A solution 8-bromo-1,2,5,6-tetrahydro-4H-pyrrolo[3,2,1-ij]quinoline (9.53 g, 40.0 mmol) in anhydrous tetrahydrofuran (317 ml) cooled to −78° C. was treated with n-butyllithium (36.1 ml, 90.1 mmol; 2.5M solution in hexanes) then stirred for 20 minutes. The reaction was treated with copper (I) cyanide (10.88 g, 120.1 mmol) then allowed to warm to between 0 and 10° C. before cooling back to −78° C. Methyl chlorooxoacetate (11.1 ml, 120.7 mmol) was added and the mixture was allowed to warm to room temperature. Water (250 ml) was added to the reaction and then the reaction was basified with saturated aqueous sodium bicarbonate. Dichloromethane (200 ml) was added and the mixture was filtered through a bed of celite. The organic layer was removed and the aqueous layer was extracted with dichloromethane (2×200 ml). The combined organic layers were dried with anhydrous sodium sulfate and evaporated to dryness to give a dark green oil which was purified by flash column chromatography (SiO$_2$, 20% EtOAc in hexanes to 25% EtOAc in hexanes) to afford oxo-(1,2,5,6-tetrahydro-4H-pyrrolo[3,2,1-ij]quinolin-8-yl)-acetic acid methyl ester as a yellow/brown solid (8.4 g). M.p=102-105° C.; 400 MHz $^1$H NMR (CDCl$_3$) δ: 7.55 (s, 1H), 7.50 (s, 1H), 3.92 (s, 3H), 3.58 (t, 2H), 3.19 (m, 2H), 3.01 (t, 2H), 2.66 (t, 2H), 2.02 (m, 2H); LCMS: 246 [M+H].

Example 13

Preparation of 3-(1H-indol-3-yl)-4-(1,2,5,6-tetrahydro-4H-pyrrolo[3,2,1-ij]quinolin-8-yl)-pyrrole-2,5-dione

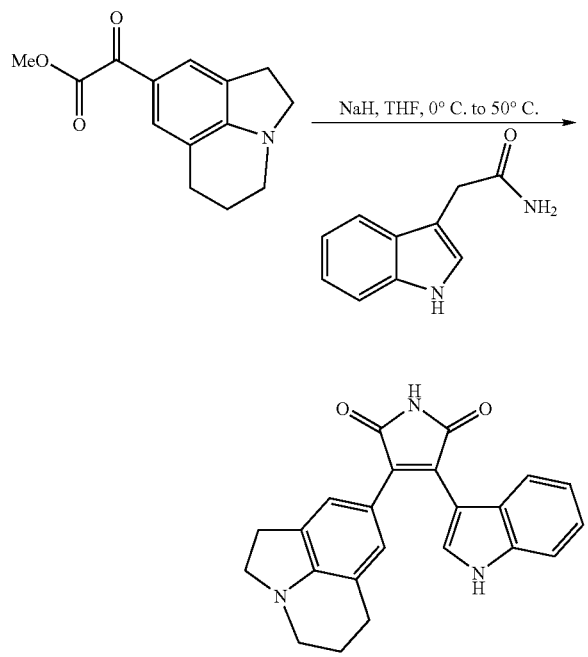

A solution of oxo-(1,2,5,6-tetrahydro-4H-pyrrolo[3,2,1-ij]quinolin-8-yl)-acetic acid methyl ester (60 mg, 0.245 mmol) and 2-(1H-indol-3-ye-acetamide (51 mg, 0.293 mmol) in anhydrous tetrahydrofuran (4 ml) at 0° C. was treated with sodium hydride (20 mg, 0.833 mmol; 95%), stirred for 5 minutes then heated to 50° C. The reaction was stirred for a further 30 minutes then cooled to 0° C. and quenched with water (5 ml) and acidified to pH6 with aqueous 2M hydrochloric acid. The mixture was extracted with dichloromethane (3×50 ml) and the combined organic extracts were dried over anhydrous sodium sulfate and evaporated to dryness. The residue was purified by flash column chromatography (SiO$_2$, 1% to 10% methanol in dichloromethane) to provide 3-(1H-indol-3-yl)-4-(1,2,5,6-tetrahydro-4H-pyrrolo[3,2,1-ij]quinolin-8-yl)-pyrrole-2,5-dione as a purple solid (60 mg). 400 MHz $^1$H NMR (CDCl$_3$) δ: 8.53 (s, 1H), 7.90 (s, 1H), 7.36 (d, J=8.2 Hz, 1H), 7.25 (m, 1H), 7.16 (m, 1H), 7.14 (m, 1H), 6.88 (t, J=7.0 Hz, 1H), 6.76 (d, J=8.2 Hz, 1H), 3.32 (t, J=7.8 Hz, 2H), 3.03 (t, J=5.5 Hz, 2H), 2.81 (t, J=8.3 Hz, 2H), 2.49 (t, J=6.7 Hz, 2H), 2.02 (m, 2H); LCMS: 370 [M+H].

Example 14

Preparation of 3-(5,6-dihydro-4H-pyrrolo[3,2,1-ij]quinolin-8-yl)-4-(1H-indol-3-yl)-pyrrole-2,5-dione

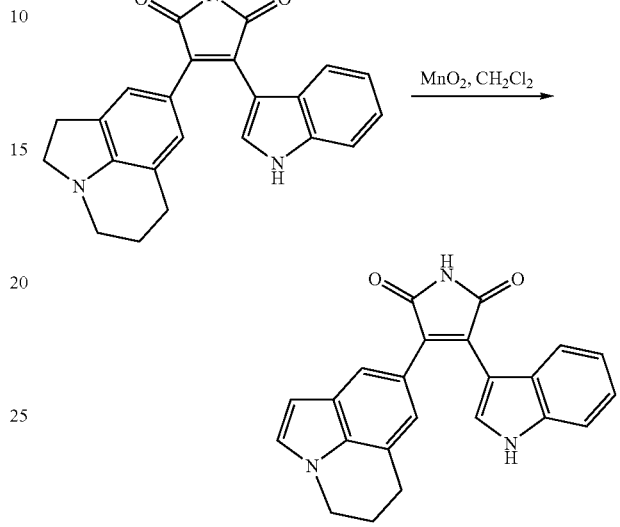

A solution of 3-(1H-indol-3-yl)-4-(1,2,5,6-tetrahydro-4H-pyrrolo[3,2,1-ij]quinolin-8-yl)-pyrrole-2,5-dione (90 mg) in dichloromethane (10 ml) at room temperature was treated with manganese dioxide (300 mg; ca. 85%, 5 μm, activated) and stirred for 1 hour. The reaction mixture was filtered through a bed of celite and the filter cake was washed with methanol (15 ml). The filtrate was evaporated to dryness and 3-(5,6-dihydro-4H-pyrrolo[3,2,1-ij]quinolin-8-yl)-4-(1H-indol-3-yl)-pyrrole-2,5-dione (88 mg) was used without further purification. 400 MHz $^1$H NMR (CDCl$_3$) δ: 8.65 (s, 1H), 7.92 (d, J=2.4 Hz, 1H), 7.73 (d, J=1.6 Hz, 1H), 7.51 (s, 1H), 7.33 (d, J=8.4 Hz, 1H), 7.07 (m, 2H), 6.70 (t, J=8.0 Hz, 1H), 6.57 (d, J=8.0 Hz, 1H), 6.38 (d, J=3.2 Hz, 1H), 4.13 (m, 2H), 2.79 (t, J=6.4 Hz, 2H), 2.16 (m, 2H); LCMS: 368 [M+H].

Example 15

Preparation of (±)-cis-3-(5,6-dihydro-4H-pyrrolo[3,2,1-ij]quinolin-8-yl)-4-(1H-indol-3-yl)-pyrrolidine-2,5-dione

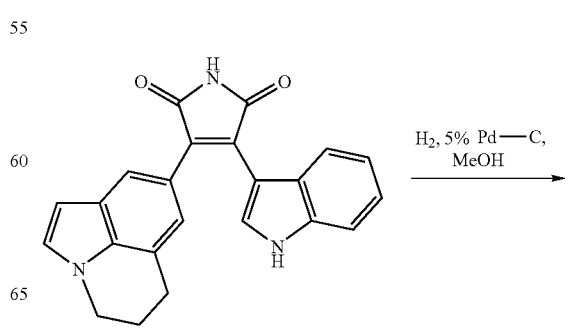

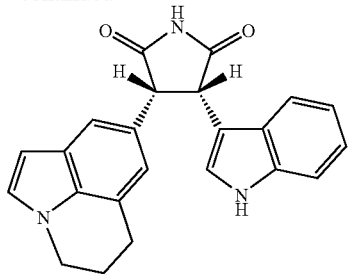

3-(5,6-dihydro-4H-pyrrolo[3,2,1-ij]quinolin-8-yl)-4-(1H-indol-3-yl)-pyrrole-2,5-dione (753 mg, 2.05 mmol) and 5% palladium on carbon (100 mg) in methanol (40 ml) were stirred under hydrogen at 60 psi for 15 hours at room temperature. The reaction mixture was filtered through a bed of celite and the filtrate evaporated to dryness to afford (±)-cis-3-(5,6-dihydro-4H-pyrrolo[3,2,1-ij]quinolin-8-yl)-4-(1H-indol-3-yl)-pyrrolidine-2,5-dione (760 mg) which was used without further purification. LCMS: 370 [M+H].

Example 16

Preparation of (±)-trans-3-(5,6-dihydro-4H-pyrrolo[3,2,1-ij]quinolin-8-yl)-4-(1H-indol-3-yl)-pyrrolidine-2,5-dione

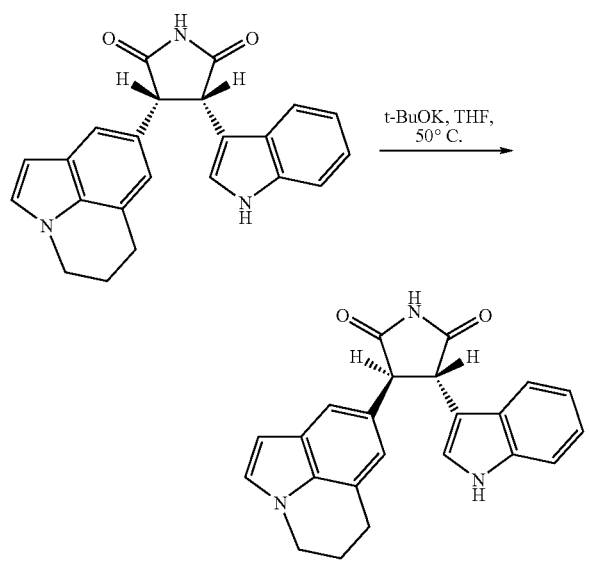

A solution of (±)-cis-3-(5,6-dihydro-4H-pyrrolo[3,2,1-ij]quinolin-8-yl)-4-(1H-indol-3-yl)-pyrrolidine-2,5-dione (760 mg, 2.06 mmol) in anhydrous tetrahydrofuran (10 ml) at room temperature was treated with potassium tert-butoxide (1.0 ml, 1.00 mmol; 1M solution in tetrahydrofuran) then heated to 50° C. and stirred for a further 1 hour. The reaction was quenched with water (10 ml) and acidified with 2M hydrochloric acid, and the mixture extracted with dichloromethane (3×50 ml). The combined organic extracts were dried over anhydrous sulfate and evaporated to dryness. The residue was purified by flash column chromatography (SiO$_2$, 1% to 10% methanol in dichloromethane) to provide (±)-trans-3-(5,6-dihydro-4H-pyrrolo[3,2,1-ij]quinolin-8-yl)-4-(1H-indol-3-yl)-pyrrolidine-2,5-dione as an orange solid (46 mg). M.p=141-145° C.; 400 MHz $^1$H NMR (CDCl$_3$) δ: 8.12 (s, 1H), 8.05 (s, 1H), 7.40 (d, J=8.2 Hz, 1H), 7.29 (s, 1H), 7.23 (m, 1H), 7.11 (m, 2H), 6.78 (s, 1H), 6.39 (d, J=2.7 Hz, 1H), 4.48 (d, J=5.9 Hz, 1H), 4.32 (d, J=5.5 Hz, 1H), 4.16 (t, J=5.5 Hz, 2H), 2.98 (t, J=6.3 Hz, 2H), 2.25 (t, J=6.3 Hz, 2H); LCMS: 370 [M+H].

Example 17

Preparation of 3-(5-bromo-1H-indol-3-yl)-4-(1,2,5,6-tetrahydro-4H-pyrrolo[3,2,1-ij]quinolin-8-yl)-pyrrole-2,5-dione To a solution of 2-(5-bromo-1H-indol-3-yl)-acetamide (500 mg, 1.98 mmol) and oxo-(1,2,5,6-tetrahydro-4H-pyrrolo[3,2,1-ij]quinolin-8-yl)-acetic acid methyl ester (404 mg, 1.65 mmol) in anhydrous tetrahydrofuran at 0° C. was added a solution of potassium tert-butoxide (4.95 ml, 4.95 mmol; 1M solution in tetrahydrofuran) dropwise over 5 minutes. The reaction was stirred for a further 30 minutes then cooled to 0° C. and quenched with water (50 ml) and acidified to pH6 with aqueous 2M hydrochloric acid. The mixture was extracted with dichloromethane (3×50 ml) and the combined organic extracts were dried over anhydrous sodium sulfate and evaporated to dryness. The residue was dissolved in N,N-dimethylformamide (4 ml) and treated with piperidine (99 μl, 1.00 mmol) and acetic acid (57 μl, 1.00 mmol). The mixture was heated to 150° C. for 5 minutes under microwave conditions then partitioned between ethyl acetate (50 ml) and water (30 ml). The aqueous layer was removed and the organic layer was washed with water (2×30 ml). The organic layer was dried over anhydrous sodium sulfate and evaporated to dryness. The residue was purified by flash column chromatography (SiO$_2$, 1% methanol to 10% methanol in dichloromethane) to provide 3-(5-bromo-1H-indol-3-yl)-4-(1,2,5,6-tetrahydro-4H-pyrrolo[3,2,1-ij]quinolin-8-yl)-pyrrole-2,5-dione as a red solid (340 mg). 400 MHz $^1$H NMR (CDCl$_3$) δ: 8.71 (s, 1H), 7.96 (d, J=2.4 Hz, 1H), 7.48 (s, 1H), 7.27 (m, 2H), 7.08 (s, 1H), 6.94 (s, 1H), 6.56 (s, 1H), 3.36 (t, J=8.0 Hz, 2H), 3.07 (m, 2H), 3.83 (t, J=8.0 Hz, 2H), 2.47 (t, J=6.8 Hz, 2H), 2.04 (m, 2H); LCMS: 448 and 450 [M+H].

Example 18

Preparation of 3-(5-bromo-1H-indol-3-yl)-4-(5,6-dihydro-4H-pyrrolo[3,2,1-ij]quinolin-8-yl-pyrrole-2,5-dione

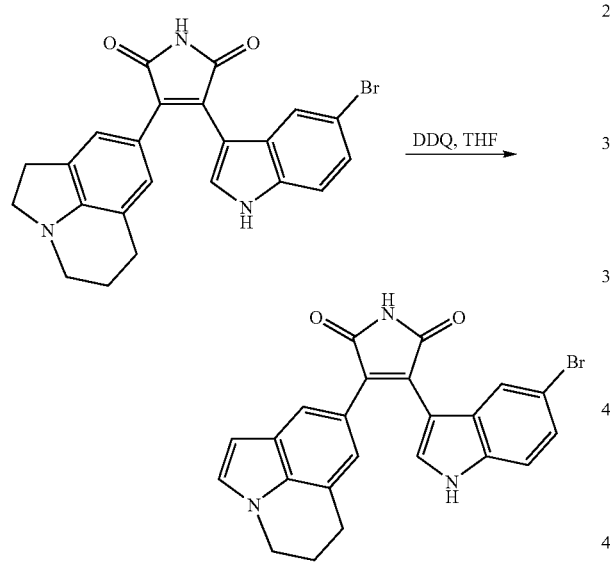

A solution of 3-(5-bromo-1H-indol-3-yl)-4-(1,2,5,6-tetrahydro-4H-pyrrolo[3,2,1-ij]quinolin-8-yl)-pyrrole-2,5-dione (300 mg, 0.668 mmol) in anhydrous tetrahydrofuran (15 ml) at room temperature was treated with 2,3-dichloro-5,6-dicyano-p-benzoquinone (182 mg, 0.802 mmol) and stirred for 30 minutes. The reaction was treated with 10% aqueous sodium sulfite (40 ml) and diluted with water (50 ml) and ethyl acetate (50 ml). The aqueous layer was removed and the organic layer was washed with saturated aqueous sodium bicarbonate (50 ml) then water (2×50 ml). The organic layer was dried over anhydrous sodium sulfate and evaporated to dryness. The residue was purified by flash column chromatography (SiO$_2$, 1% methanol to 10% methanol in dichloromethane) to provide 3-(5-bromo-1H-indol-3-yl)-4-(5,6-dihydro-4H-pyrrolo[3,2,1-ij]quinolin-8-yl)-pyrrole-2,5-dione as an orange solid (255 mg). 400 MHz $^1$H NMR (DMSO-d$_6$) δ: 11.94 (s, 1H), 10.95 (s, 1H), 7.99 (s, 1H), 7.45 (d, J=1.6 Hz, 1H), 7.33 (m, 2H), 7.08 (dd, J=6.8 and 1.6 Hz, 1H), 6.81 (d, J=1.6 Hz, 1H), 6.34 (d, J=2.8 Hz, 1H), 6.20 (d, J=2.0 Hz, 2H), 4.17 (m, 2H), 2.75 (m, 2H), 2.12 (m, 2H); LCMS: 446 and 448 [M+H].

Example 19

Preparation of (±)-trans-3-(5-bromo-1H-indol-3-yl)-4-(5,6-dihydro-4H-pyrrolo[3,2,1-ij]quinolin-8-yl)-pyrrolidine-2,5-dione

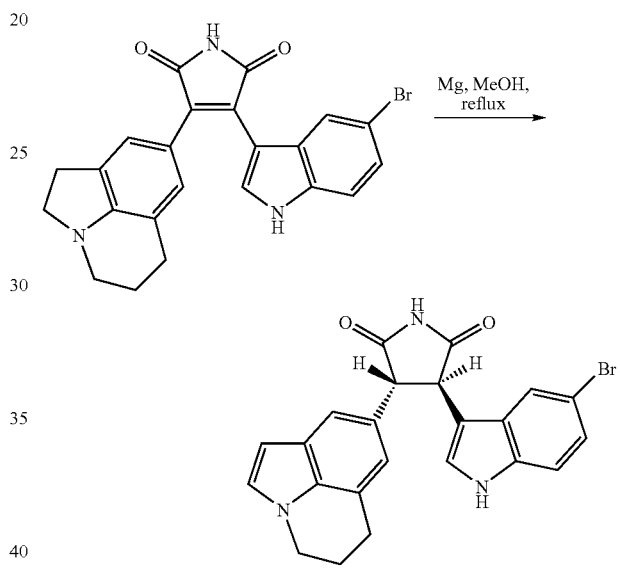

To a solution of 3-(5-bromo-1H-indol-3-yl)-4-(5,6-dihydro-4H-pyrrolo[3,2,1-ij]quinolin-8-yl)-pyrrole-2,5-dione (250 mg, 0.559 mmol) in methanol (35 ml) was added magnesium turnings (354 mg, 14.57 mmol) portionwise over 20 minutes and the mixture was heated to reflux for 6 hours. The mixture was cooled and diluted with water (50 ml) and acidified with 2M aqueous hydrochloric acid. The mixture was extracted with dichloromethane (3×50 ml) and the combined organic extracts were dried over anhydrous sodium sulfate and evaporated to dryness. The residue was purified (Xterra C18, reverse phase column, eluted with acetonitrile-water system with 0.1% trifluoracetic acid as modifier) to provide (±)-trans-3-(5-bromo-1H-indol-3-yl)-4-(5,6-dihydro-4H-pyrrolo[3,2,1-ij]quinolin-8-yl)-pyrrolidine-2,5-dione as a brown solid (45 mg). M.p.=195-200° C.; 400 MHz $^1$H NMR (DMSO-d$_6$) δ: 11.41 (s, 1H), 11.24 (s, 1H), 7.99 (d, J=2.0 Hz, 1H), 7.47 (d, J=2.0 Hz, 1H), 7.30 (m, 3H), 7.17 (dd, J=8.4 and 2.0 Hz, 1H), 6.83 (s, 1H), 4.53 (d, J=7.6 Hz, 1H), 4.38 (d, J=7.6 Hz, 1H), 4.13 (m, 2H), 2.90 (t, J=6.0 Hz, 2H), 2.11 (m, 2H); LCMS: 448 and 450 [M+H].

Example 20

Preparation of 3-(2-chloro-phenyl)-4-(1,2,5,6-tetrahydro-4H-pyrrolo[3,2,1-ij]quinolin-8-yl-pyrrole-2,5-dione

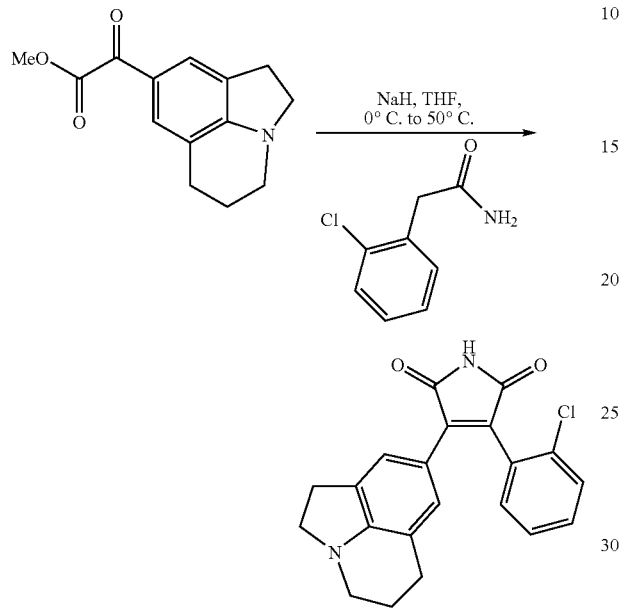

3-(2-Chloro-phenyl)-4-(1,2,5,6-tetrahydro-4H-pyrrolo[3,2,1-ij]quinolin-8-yl)-pyrrole-2,5-dione was prepared according to example 13 employing 2-(2-chloro-phenyl)-acetamide in place of 2-(1H-indol-3-yl)-acetamide. 400 MHz $^1$H NMR (CDCl$_3$) δ: 7.70 (s, 1H), 7.48 (d, J=7.6 Hz, 1H), 7.31 (m, 3H), 7.13 (s, 1H), 7.08 (s, 1H), 3.38 (t, J=8.4 Hz, 2H), 3.06 (m, 2H), 2.85 (t, J=7.6 Hz, 2H), 2.53 (t, J=6.8 Hz, 2H), 1.99 (m, 2H); LCMS: 365 [M+H].

Example 21

Preparation of 3-(2-chloro-phenyl)-4-(5,6-dihydro-4H-pyrrolo[3,2,1-ij]quinolin-8-yl-pyrrole-2,5-dione

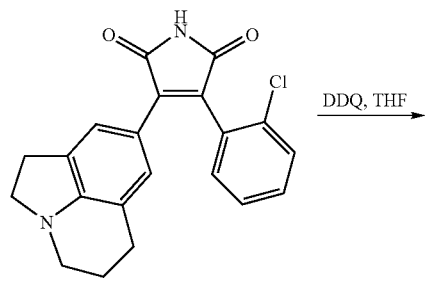

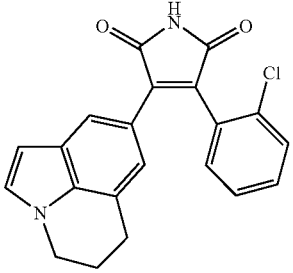

3-(2-Chloro-phenyl)-4-(5,6-dihydro-4H-pyrrolo[3,2,1-ij]quinolin-8-yl)-pyrrole-2,5-dione was prepared according to example 18 employing 3-(2-chloro-phenyl)-4-(1,2,5,6-tetrahydro-4H-pyrrolo[3,2,1-ij]quinolin-8-yl)-pyrrole-2,5-dione in place of 3-(5-bromo-1H-indol-3-yl)-4-(1,2,5,6-tetrahydro-4H-pyrrolo[3,2,1-ij]quinolin-8-yl)-pyrrole-2,5-dione. 400 MHz $^1$H NMR (CDCl$_3$) δ: 7.68 (s, 1H), 7.56 (s, 1H), 7.48 (d, J=7.6 Hz, 1H), 7.37 (t, J=7.6 Hz, 1H), 7.28 (m, 2H), 7.06 (d, J=3.2 Hz, 1H), 6.97 (s, 1H), 6.40 (d, J=2.8 Hz, 1H), 4.12 (t, J=5.6 Hz, 2H), 2.86 (t, J=5.2 Hz, 2H), 2.19 (m, 2H); LCMS: 363 [M+H].

Example 22

Preparation of (±)-trans-3-(2-chloro-phenyl)-4-(5,6-dihydro-4H-pyrrolo[3,2,1-ij]quinolin-8-yl)-pyrrolidine-2,5-dione

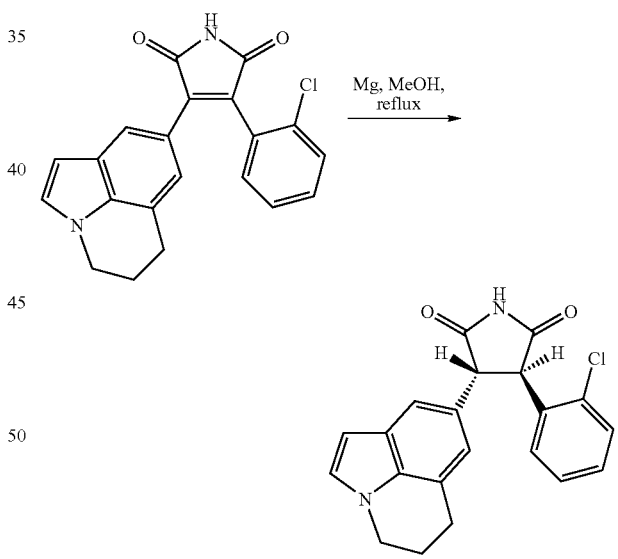

(±)-trans-3-(2-Chloro-phenyl)-4-(5,6-dihydro-4H-pyrrolo[3,2,1-ij]quinolin-8-yl)-pyrrolidine-2,5-dione was prepared according to example 19 employing 3-(2-chloro-phenyl)-4-(5,6-dihydro-4H-pyrrolo[3,2,1-ij]quinolin-8-yl)-pyrrole-2,5-dione in place of 3-(5-bromo-1H-indol-3-yl)-4-(5,6-dihydro-4H-pyrrolo[3,2,1-ij]quinolin-8-yl)-pyrrole-2,5-dione. M.p.=209-212° C.; 400 MHz $^1$H NMR (DMSO-d$_6$) δ: 11.59 (s, 1H), 7.47 (dd, J=7.6 and 1.2 Hz, 1H), 7.33 (m, 4H), 7.20 (d, J=1.2 Hz, 1H), 6.79 (s, 1H), 6.28 (d, J=2.8 Hz, 1H), 4.61 (d, J=7.6 Hz, 1H), 4.25 (d, J=7.2 Hz, 1H), 4.14 (t, J=5.6 Hz, 2H), 2.90 (t, J=6.0 Hz, 2H), 2.11 (m, 2H); LCMS: 365 [M+H].

Example 23

Preparation of 3-(3-methoxy-phenyl)-4-(1,2,5,6-tetrahydro-4H-pyrrolo[3,2,1-ij]quinolin-8-yl)-pyrrole-2,5-dione

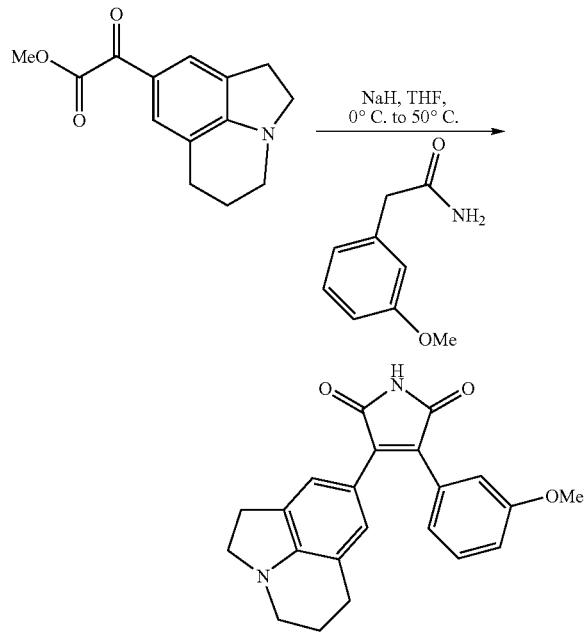

3-(3-Methoxy-phenyl)-4-(1,2,5,6-tetrahydro-4H-pyrrolo[3,2,1-ij]quinolin-8-yl)-pyrrole-2,5-dione was prepared according to example 13 employing 2-(3-methoxy-phenyl)-acetamide in place of 2-(1H-indol-3-yl)-acetamide. 400 MHz ¹H NMR (CDCl₃) δ: 7.63 (m, 2H), 7.24 (m, 1H), 7.11 (d, J=10.8 Hz, 1H), 7.07 (m, 2H), 6.90 (d, J=7.2 Hz, 1H), 3.76 (s, 3H), 3.46 (t, J=8.0 Hz, 1H), 3.38 (t, J=8.0 Hz, 1H), 3.11 (m, 1H), 3.06 (m, 1H), 2.98 (t, J=8.4 Hz, 1H), 2.87 (t, J=8.4 Hz, 1H), 2.68 (t, J=6.0 Hz, 1H), 2.59 (t, J=6.0 Hz, 1H); LCMS: 361 [M+H].

Example 24

Preparation of 3-(5,6-dihydro-4H-pyrrolo[3,2,1-ij]quinolin-8-yl)-4-(3-methoxy-phenyl)-pyrrole-2,5-dione

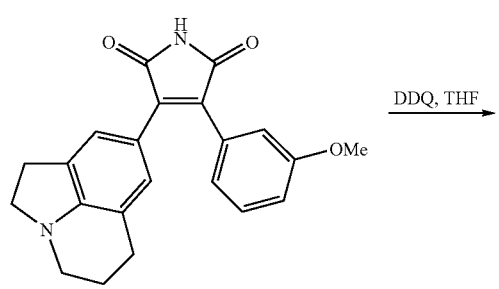

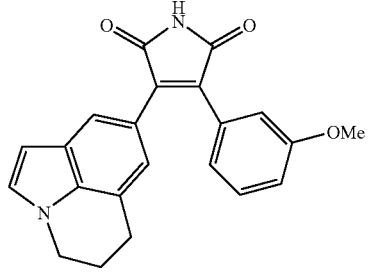

3-(5,6-dihydro-4H-pyrrolo[3,2,1-ij]quinolin-8-yl)-4-(3-methoxy-phenyl)-pyrrole-2,5-dione was prepared according to example 18 employing 3-(3-methoxy-phenyl)-4-(1,2,5,6-tetrahydro-4H-pyrrolo[3,2,1-ij]quinolin-8-yl)-pyrrole-2,5-dione in place of 3-(5-bromo-1H-indol-3-yl)-4-(1,2,5,6-tetrahydro-4H-pyrrolo[3,2,1-ij]quinolin-8-yl)-pyrrole-2,5-dione. 400 MHz ¹H NMR (CDCl₃) δ: 7.69 (d, J=1.2 Hz, 1H), 7.34 (s, 1H), 7.23 (t, J=8.0 Hz, 1H), 7.09 (m, 2H), 7.06 (d, J=8.0 Hz, 1H), 6.99 (d, J=1.2 Hz, 1H), 6.91 (d, J=2.4 Hz, 1H), 6.44 (d, J=2.8 Hz, 1H), 4.15 (m, 2H), 3.71 (s, 3H), 2.91 (t, J=6.4 Hz, 2H), 2.22 (m, 2H); LCMS: 359 [M+H].

Example 25

Preparation of (±)-trans-3-(5,6-dihydro-4H-pyrrolo[3,2,1-ij]quinolin-8-yl)-4-(3-methoxy-phenyl)-pyrrolidine-2,5-dione

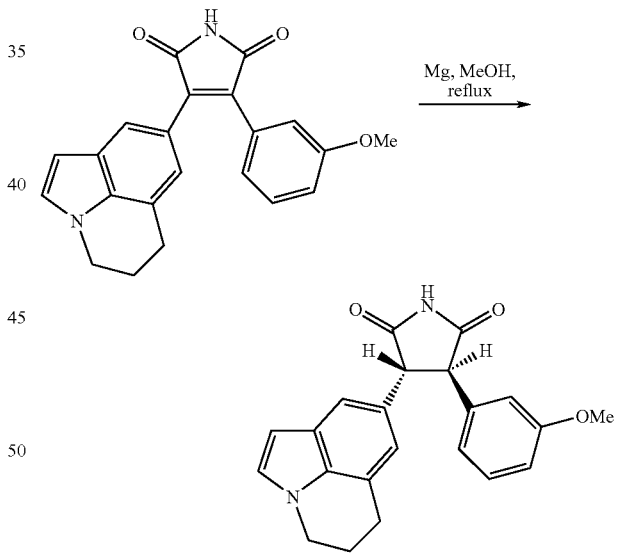

(±)-trans-3-(5,6-dihydro-4H-pyrrolo[3,2,1-ij]quinolin-8-yl)-4-(3-methoxy-phenyl)-pyrrolidine-2,5-dione was prepared according to example 19 employing 3-(5,6-dihydro-4H-pyrrolo[3,2,1-ij]quinolin-8-yl)-4-(3-methoxy-phenyl)-pyrrole-2,5-dione in place of 3-(5-bromo-1H-indol-3-yl)-4-(5,6-dihydro-4H-pyrrolo[3,2,1-ij]quinolin-8-yl)-pyrrole-2,5-dione. 400 MHz ¹H NMR (DMSO-d₆) δ: 11.44 (s, 1H), 7.30 (d, J=2.8 Hz, 1H), 7.23 (d, J=8.0 Hz, 1H), 7.20 (s, 1H), 6.89 (m, 1H), 6.85 (m, 1H), 6.77 (s, 1H), 6.29 (d, J=3.2 Hz, 1H), 4.32 (d, J=8.0 Hz, 1H), 4.27 (d, J=7.6 Hz, 1H), 4.13 (m, 2H), 3.72 (s, 3H), 2.90 (t, J=6.0 Hz, 2H), 2.11 (m, 2H); LCMS: 359 [M+H].

Example 26

Preparation of 1-nitroso-2,3-dihydro-1H-indole

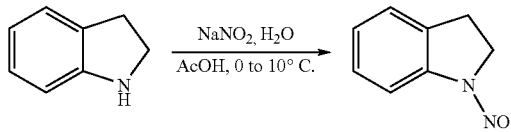

To a solution of 2,3-dihydro-1H-indole (10.0 g, 84 mmol) in acetic acid (100 ml) at 0° C. was added dropwise a solution of sodium nitrite (6.08 g, 88 mmol) in water (25 ml) so that the temperature was maintained below 5° C. After 1 hour water (500 ml) and 1 M hydrochloric acid (500 ml) were added to the precipitate that formed. The mixture was stirred for another hour before the product was filtered off, washed with water (3×100 ml) and dried under vacuum to give 1-nitroso-2,3-dihydro-1H-indole as a brown solid (5.27 g). 400 MHz $^1$H NMR (DMSO-$d_6$) δ: 7.8 (d, J=7.6 Hz 1H), 7.45 (d, J=7.6 Hz, 1H), 7.37 (t, J=7.6 Hz 1H), 7.29 (t, J=7.6 Hz, 1H), 4.09 (m, 2H), 3.19 (t, J=7.6 Hz, 2H); LCMS: 149 [M+H]

Example 27

Preparation of 2,3-dihydro-indol-1-ylamine

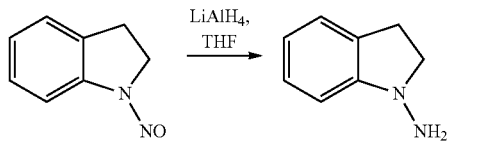

A solution of 1-nitroso-2,3-dihydro-1H-indole (5.27 g, 35.6 mmol) in tetrahydrofuran (35 ml) was added dropwise to a refluxing slurry of lithium aluminium hydride (2.98 g, 78.5 mmol) in tetrahydrofuran (100 ml). After 1 hour the mixture was cooled in an ice bath and water (3 ml) carefully added. 2M sodium hydroxide (6 ml) followed by water (6 ml) were added and the mixture heated to reflux for 30 minutes. After cooling to room temperature the precipitate formed was filtered off. The filtrate obtained was evaporated to dryness to yield 2,3-dihydro-indol-1-ylamine as a red/brown oil (4.216 g), which was used for the next step without further purification.

Example 28

Preparation of 4,5-dihydro-pyrrolo[3,2,1-hi]indole-2-carboxylic acid ethyl ester

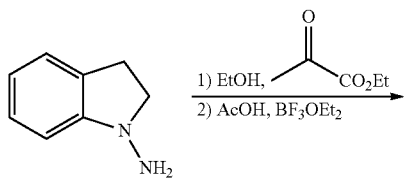

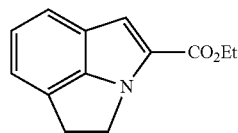

Ethyl pyruvate (3.7 ml, 33.3 mmol) was added to a solution of 2,3-dihydro-indol-1-ylamine (4.216 g, 31.4 mmol) in absolute ethanol (40 ml). The mixture was heated to reflux for 1 hour before being evaporated to dryness. The residue was dissolved in acetic acid (40 ml) and boron trifluoride etherate (4.0 ml 31.4 mmol) added. The mixture was heated to reflux for 1 hour then poured into ethyl acetate (200 ml). The ethyl acetate was washed with water (1 L), saturated sodium hydrogen carbonate (2×300 ml) and brine (100 ml). After drying over anhydrous magnesium sulfate the mixture was evaporated to dryness and the residue purified by flash column chromatography ($SiO_2$, 7% to 10% EtOAc in hexanes) to afford 4,5-dihydro-pyrrolo[3,2,1-hi]indole-2-carboxylic acid ethyl ester as a yellow solid (1.117 g). 400 MHz $^1$H NMR (DMSO-$d_6$) δ: 7.35 (d, J=6.8 Hz, 1H), 7.12 (s, 1H), 7.04-6.99 (m, 2H), 4.73 (t, J=6.8 Hz, 2H), 4.37 (q, J=7.2 Hz, 2H), 3.77 (t, J=6.8 Hz, 2H), 1.41 (t, 6.8 Hz, 3H); LCMS: 216 [M+H].

Example 29

Preparation of 4,5-dihydro-pyrrolo[3,2,1-hi]indole-2-carboxylic acid

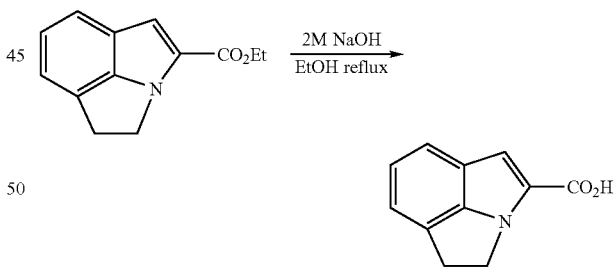

A solution of 4,5-dihydro-pyrrolo[3,2,1-hi]indole-2-carboxylic acid ethyl ester (1.117 g) in ethanol (25 ml) and 2M sodium hydroxide (25 ml) was heated to reflux for 1 hour. The mixture was cooled to room temperature and poured into water (300 ml). 1M hydrochloric acid was added until pH1 and the precipitate formed filtered off and washed with water (50 ml). After drying under reduced pressure 4,5-dihydro-pyrrolo[3,2,1-hi]indole-2-carboxylic acid was obtained as a pale yellow powder (884 mg). 400 MHz $^1$H NMR (DMSO-$d_6$) δ: 12.94 (s, 1H), 7.31 (d, J=7.2 Hz, 1H), 7.01-6.96 (m, 3H), 4.67 (t, J=6.8 Hz, 2H), 3.74 (t, J=6.8 Hz, 2H); LCMS: 188 [M+H].

Example 30

Preparation of 1,2-dihydro-pyrrolo[3,2,1-hi]indole

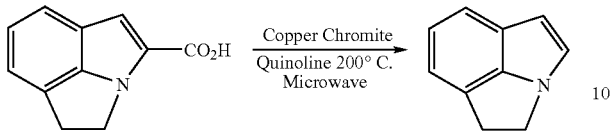

A mixture of 4,5-dihydro-pyrrolo[3,2,1-hi]indole-2-carboxylic acid (120 mg, 0.64 mmol) and copper chromite (50 mg) in quinoline (5 ml) in a sealed vessel was heated to 200° C. in a microwave for 20 minutes. After cooling to room temperature the mixture was poured into ethyl acetate (100 ml) and washed with 1M hydrochloric acid (3×100 ml). The organic layer was dried over anhydrous magnesium sulfate and evaporated to dryness. The residue was purified by preparative thin layer chromatography (SiO$_2$, 20% EtOAc in hexanes) to yield 1,2-dihydro-pyrrolo[3,2,1-hi]indole as a pale yellow crystalline solid (56 mg). 400 MHz $^1$H NMR (CDCl$_3$) δ: 7.33 (d, J=8.0 Hz, 1H), 7.14 (d, J=2.8 Hz, 1H), 7.04-6.97 (m, 1H), 6.91 (d, J=6.8 Hz, 1H), 6.44 (d, J=2.8 Hz, 1H), 4.51 (t, J=7.2 Hz, 2H), 3.80 (t, J=7.2 Hz, 2H); LCMS: 144 [M+H].

Example 31

Preparation of (4,5-dihydro-pyrrolo[3,2,1-hi]indol-1-yl)-oxo-acetic acid methyl ester

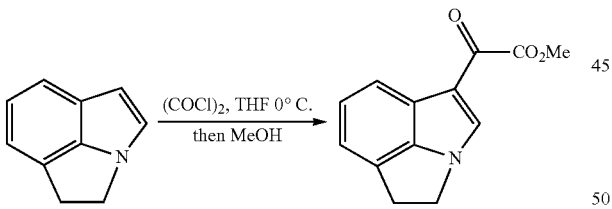

To a solution of 1,2-dihydro-pyrrolo[3,2,1-hi]indole (112 mg, 0.78 mmol) in anhydrous tetrahydrofuran (3 ml) at 0° C. was added oxalyl chloride (71 μl, 0.82 mmol). The mixture was stirred at 0° C. for 1 hour. Methanol (1 ml) was added and the mixture was allowed to warm to room temperature. After 30 minutes ethyl acetate (100 ml) was added and the mixture washed with water (100 ml) and brine (50 ml). The organic layer was dried over anhydrous magnesium sulfate and evaporated to dryness to give (4,5-dihydro-pyrrolo[3,2,1-hi]indol-1-yl)-oxo-acetic acid methyl ester as a purple solid (153 mg). 400 MHz $^1$H NMR (CDCl$_3$) δ: 8.32 (s, 1H), 7.86 (d, J=7.6 Hz, 1H), 7.23 (d, J=8.0 Hz, 1H), 7.08 (d, J=6.4 Hz, 1H), 4.60 (t, J=6.8 Hz, 2H), 3.95 (s, 3H), 3.84 (t, J=6.8 Hz, 2H); LCMS: 230 [M+H].

Example 32

Preparation of 3-(4,5-dihydro-pyrrolo[3,2,1-hi]indol-1-yl)-4-(1H-indol-3-yl)-pyrrole-2,5-dione

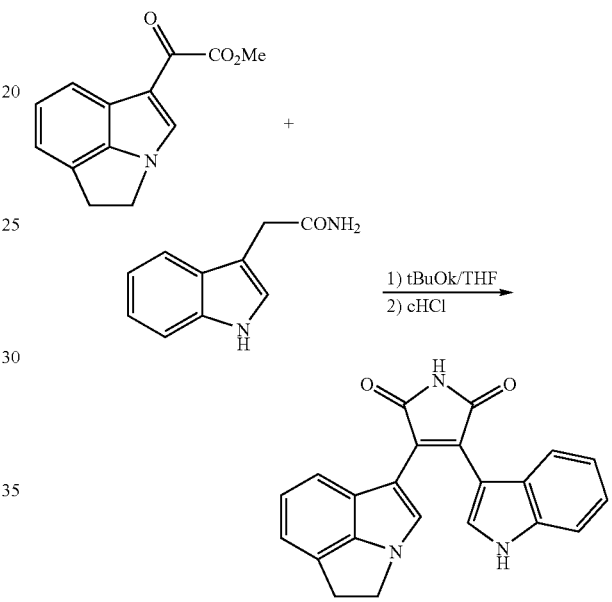

To a solution of (4,5-dihydro-pyrrolo[3,2,1-hi]indol-1-yl)-oxo-acetic acid methyl ester (150 mg, 0.66 mmol) and 2-(1H-indol-3-yl)-acetamide (114 mg, 0.66 mmol) in anhydrous tetrahydrofuran (10 ml) at 0° C. was added potassium tert-butoxide (2.6 ml, 2.6 mmol; 1M solution in tetrahydrofuran). The mixture was stirred at room temperature for 1 hour before concentrated hydrochloric acid (3 ml) was added and the mixture stirred for an additional 20 minutes. The mixture was poured into ethyl acetate (200 ml) washed with water (700 ml) and brine (100 ml). The organic layer was dried over anhydrous sodium sulfate and evaporated to dryness. The residue was purified by flash column chromatography (SiO$_2$, 40% EtOAc in hexanes) to afford 3-(4,5-dihydro-pyrrolo[3,2,1-hi]indol-1-yl)-4-(1H-indol-3-yl)-pyrrole-2,5-dione as a red solid (115 mg). 400 MHz $^1$H NMR (DMSO-d$_6$) δ: 11.63 (s, 1H), 10.84 (s, 1H), 7.98 (s, 1H), 7.62 (d, J=2.8 Hz, 1H), 7.42 (d, J=8.0 Hz, 1H), 7.05-7.01 (m, 2H), 6.78-6.74 (m, 2H), 6.53 (t, J=7.2 Hz, 1H), 6.08 (d, J=8.0 Hz, 1H), 4.58 (t, J=7.2 Hz, 2H), 3.71 (t, J=6.8 Hz, 2H); LCMS: 354 [M+H].

Example 33

Preparation of (±)-trans-3-(4,5-dihydro-pyrrolo[3,2,1-hi]indol-1-yl)-4-(1H-indol-3-yl)-pyrrolidine-2,5-dione

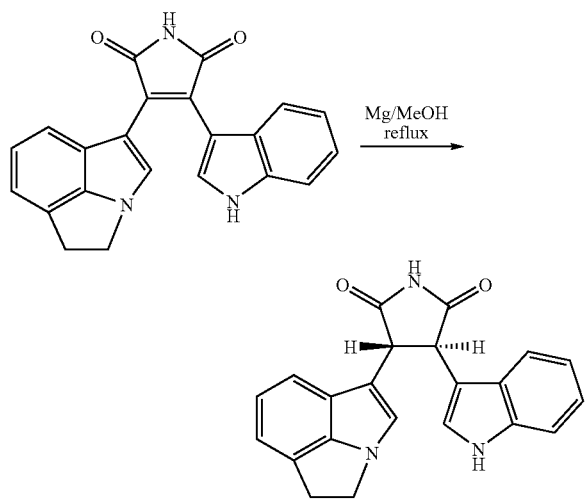

To a solution of 3-(4,5-dihydro-pyrrolo[3,2,1-hi]indol-1-yl)-4-(1H-indol-3-yl)-pyrrole-2,5-dione (115 mg, 0.33 mmol) in anhydrous methanol (10 ml) was added magnesium turnings (200 mg). The mixture was heated to reflux for 1.5 hours. The mixture was cooled to room temperature poured into ethyl acetate (100 ml) washed with 1M hydrochloric acid (100 ml) and dried over anhydrous magnesium sulfate. Evaporation to dryness gave a residue that was purified by flash column chromatography (SiO$_2$, 50% EtOAc in hexanes) to yield (±)-trans-3-(4,5-dihydro-pyrrolo[3,2,1-hi]indol-1-yl)-4-(1H-indol-3-yl)-pyrrolidine-2,5-dione as a pink solid (108 mg). M.p.=144-148° C., 400 MHz $^1$H NMR (DMSO-d$_6$) δ: 11.53 (s, 1H), 11.05 (s, 1H), 7.41-7.35 (m, 4H), 7.14-7.07 (m, 2H), 6.96 (t, J=7.6 Hz, 1H), 6.89-6.85 (m, 2H), 4.51-4.45 (m, 4H), 3.69 (t, J=7.2 Hz, 2H); LCMS: 356 [M+H].

Example 34

Exponentially growing HT29 cells were plated in black 96-well plates at 5,000 cells/well overnight in medium with 10% FBS. The next day, cells were transiently transfected for 2 days using DharmaFECT 4 reagent with a pool of four met-specific 21-nucleotide RNA oligonucleotides forming a 19-bp duplex core with 2-nucleotide 3' overhang in combination (Dharmacon, Inc., Lafayette, Colo.). Transfection of gapdh siRNA (Dharmacon, Inc.) and of a non-targeting siRNA under the same conditions was done in parallel as controls (Dharmacon, Inc.). Cells were then incubated in the absence or the presence of increasing concentrations of ZvAD-FMK, an irreversible caspase inhibitor for 1 additional day. Cells were incubated for at least 10 minutes in a labeling solution (10 mM HEPES, 140 mM NaCl and 6 mM CaCl$_2$) containing 2 µg/ml Hoechst 33342 (blue channel; Molecular Probes/Invitrogen Corp., Natick, Mass.), 500 times diluted Annexin V-Fluos (green channel; Roche Applied Science, Indianapolis, Ind.) and 1 µg/ml propidium iodide (red channel; Roche Applied Science). High content image acquisition and analysis were carried out using a Beckman Coulter IC100 Cytometer. The program was set to take four images per well. The exposure time was set at 16.7 ms/10% gain, 500 ms/35% gain, and 300 ms/30% gain for DAPI, FITC and Rhodamine channel respectively. Images were processed and numbers of positive cells for each channel and each condition were determined using Cytoshop 2.1 software (Beckman Coulter, Inc.). An increased amount of cell death, determined by the percentage of cells positively stained by Annexin V-Fluos, was observed in HT29 cells transfected with met siRNA, as compared with the controls (gapdh and non-targeting siRNA transfected cells). Furthermore, presence of increased concentrations of ZvAD-FMK decreased the levels of cell death indicating that c-Met knockdown induces caspase-dependent apoptosis in HT29 cells. These data further indicate that HT29 cells are at least partly dependent upon c-Met the pathway for their survival and, hence, are a good model to test for c-Met inhibitor compounds. See, e.g., FIG. 1A.

The same experiment was done using the exact same conditions in parallel to check for effective knockdown of GAPDH and c-Met using siRNA in HT29 cells. After 3 days transfection, whole-cell extracts were prepared in Cell Lysis Buffer (Cell Signaling Technology) containing 20 mM Tris-HCl [pH 7.5], 150 mM NaCl, 1 mM Na$_2$EDTA, 1 mM EGTA, 1% Triton, 2.5 mM sodium pyrophosphate, 1 mM β-glycerophosphate, 1 mM Na$_3$VO$_4$, 1 µg/ml leupeptin and 1 mM PMSF. The protein concentration was measured by Bradford assay by using the Bio-Rad reagent (Bio-Rad, Hercules, Calif.) according to the manufacturer's directions. Samples (50 µg of total protein) were resolved by SDS-7.5% polyacrylamide gel electrophoresis (PAGE) under reducing conditions and transferred onto polyvinylidene difluoride membranes (Millipore Corp., Billerica, Mass.). The membranes were incubated overnight at 4° C. in TBS-T (50 mM Tris-HCl [pH 7.6], 200 mM NaCl, 0.1% Tween 20) with 3% bovine serum albumin. c-Met, GAPDH and β-actin expression levels were determined by incubating the membranes with a rabbit polyclonal anti-c-Met antibody (sc-10; Santa Cruz Biotechnology, Santa Cruz, Calif.), and monoclonal antibodies against GAPDH (Dharmacon, Inc.) and β-actin (Invitrogen Corp, Carlsbad, Calif.) in TBS-T with 3% bovine serum albumin. After an extensive washing in TBS-T, a 1:5,000 dilution of secondary horseradish peroxidase-conjugated antibody (Amersham Biosciences Corp., Piscataway, N.J.) was added for 1 h, and specific protein bands were visualized by using an enhanced chemiluminescence detection system (PerkinElmer Detection Systems, Woburn, Mass.) according to the manufacturer's instructions. See, e.g., FIG. 1B.

cDNA of full-length c-Met purchased from Origen Technologies was used as template for PCR amplification. The DNA fragment encoding the kinase domain (1038-1346) was inserted into Novagen vector pet28a between Nco1 and Sal1 sites. The primers were designed to contain a six-histidine tag to the N-terminus. In order to express dephosphorylated c-Met kinase protein, a tyrosine phosphatase PTP1B (1-283) was sequentially ligated into the made construct between SalI and Nod sites. A second ribosome binding site was incorporated in the PTP1B primer after the SalI site. The N-terminal His-tagged proteins were expressed in Circlegrow broth (Q-Biogen). The transformed E. Coli cell line BL21(DE3) RIL (Stratagene) was cultured to OD=0.8 at 37° C. and induced with 0.3 mM of IPTG for overnight at 12° C. The co-expressed protein was purified by metal-chelation chromatography followed by anion and cation columns. In brief, 4 liters of cells were lysed by sonication in 140 ml buffer containing 20 mM MOPS pH=6.5, 200 mM NaCl, 7.5% glycerol, 0.1% Igepal, supplied with 1 mM PMSF. The supernatant was obtained by centrifugation at 50,000 g for 30 minutes and followed by incubation with 8 mL of Ni-NTA His Bind resin (Novagen) at 4° C. for one hour. A second step 50 mL wash buffer (with 100 mM NaCl and 5 mM imidazole) was applied after initial wash with the lysis buffer. Protein was eluted by 200 mM imidazole pH=8.5, 100 mM NaCl and 7.5% glycerol and directly cleared by passing 10 mL QFF column. The salt concentration and the pH value of the protein flow through were adjusted to 50 mM and 7.5 by dilution, and then loaded to 1 mL SP FF column. The protein was further gel-filtered in an equilibrium buffer of 20 mM TrisHCl pH=8.5, 150 mM NaCl, 7.5% glycerol and 2 mM DTT. The monomeric unphosphorylated c-Met protein was concentrated to 30 mg/mL for storage at −80° C.

Recombinant unphosphorylated c-Met comprising residues 1038-1346 (12.5 ng) was pre-incubated with increasing concentrations of compounds for 15 minutes at room temperature. Following preincubation with compounds, 100 μM of IGF-1 Rtide substrate and 100 μM ATP containing 2.5 μCi [$^{33}$P-γATP] was added to the mixture. The reaction was carried out for 30 minutes in a Reaction Buffer containing 8 mM MOPS-NaOH pH=7.0, 200 μM EDTA, 5 mM Magnesium acetate, 200 μM dithiothreitol (DTT) and 10 mM Na$_3$VO$_4$. The reaction was then terminated with 10 μL of 3% phosphoric acid. Ten μL were transferred onto a filterplate and were washed 3-times with 1% phosphoric acid; counts were read with a microbeta counter, and IC$_{50}$ for c-Met inhibition was determined for each compound.

Example 35

MTS Assay

HT29 cells were seeded in 96-well plates at 1,800 cells/well overnight in medium with 10% FBS. The next day, cells were treated with increasing concentrations of compounds for 24 hours at 37° C. After the treatments, the compound-containing medium was removed, cells were washed twice with PBS, and incubated in drug-free medium containing 10% FBS for an additional 48 hours. After addition of MTS and PMS for 4 hours at concentrations of 2 mg/mL and 0.92 mg/mL, respectively, the results were quantitated by spectrophotometry at λ=490 nm and IC$_{50}$ for each compound was determined

| Example Number | HT-29; IC$_{50}$ | c-Met; p33 assay; IC$_{50}$ |
|---|---|---|
| 6 | B | |
| 9 | B | C |
| 16 | A | C |
| 19 | A | |
| 22 | A | |
| 25 | A | |
| 33 | A | C |

A ≦ 1 μM;
B = 1-10 μM;
C ≧ 10 μM

Other embodiments were within the following claims. While several embodiments have been shown and described, various modifications may be made without departing from the spirit and scope of the present invention.

What is claimed is:

1. A compound of formula Ia, Ib, IIa, or IIb, or a pharmaceutically acceptable salt thereof:

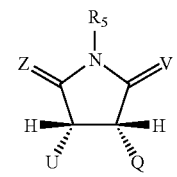
(Ia)

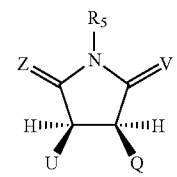
(Ib)

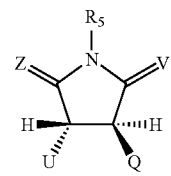
(IIa)

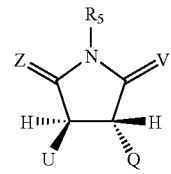
(IIb)

Where U is independently selected from:

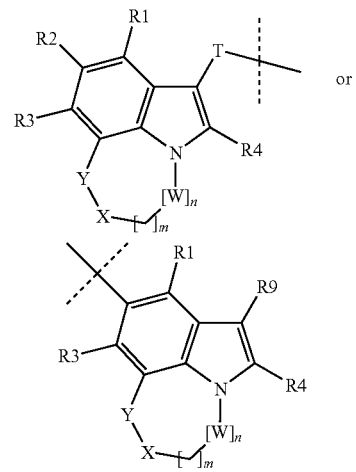

wherein:
R1, R2, and R3 are independently selected from the group consisting of H, F, Cl, Br, I, —NR7R8, —(C$_1$-C$_6$) substituted alkyl, —(C$_3$-C$_9$)cycloalkyl, —(C$_3$-C$_9$) substituted cycloalkyl, —O—(C$_1$-C$_6$) alkyl, —O—(C$_3$-C$_9$) cycloalkyl, and —O—(C$_3$-C$_9$) substituted cycloalkyl, aryl, heteroaryl, and heterocyclyl;
R4, R7, and R8 are independently selected from the group consisting of H, —(C$_1$-C$_4$) alkyl, and —(C$_1$-C$_4$) substituted alkyl;
R5 is selected from the group consisting of H, —(C$_1$-C$_6$) alkyl, and —CH$_2$R6;
R6 is selected from the group consisting of —O—P(═O)(OH)$_2$, —O—P(═O)(—OH)(—O—(C$_1$-C$_6$) alkyl), —O—P(=O)(—O—(C₁-C₆ alkyl)₂, —O—P(=O)(—OH) (—O—(CH₂)-phenyl), —O—P(=O)(—O—(CH₂)-phenyl)₂, a carboxylic acid group, an amino carboxylic acid group, and a peptide;

R9 is selected from the group consisting of H, —(C₁-C₆) alkyl, —(C₁-C₆) substituted alkyl, —(C₃-C₉)cycloalkyl, —(C₃-C₉) substituted cycloalkyl, aryl, heteroaryl, and heterocyclyl;

Q is selected from the group consisting of aryl, heteroaryl, heterocyclyl, alkyl, substituted aryl, substituted heteroaryl, substituted heterocyclyl, and substituted alkyl;

T is —CH₂—, —C(O)—, or a bond; when T is a bond, then Y is a bond, W is bond, X is —CH₂—, and m=1, n=0;

V and Z are independently selected from the group consisting of O, S, and H₂;

X is —CH₂—;

Y and W are independently —CH₂—, or a bond;

m is 1 or 2;

n is 1 or 2.

2. The compound of claim 1, wherein Q is an indolyl group or an indolyl group substituted with one or more substituents independently selected from the group consisting of: F, Cl, Br, I, —(C₁-C₆)alkyl, —(C₁-C₆)fluoro-substituted alkyl, —(C₃-C₉)cycloalkyl, —(C₃-C₉)fluoro-substituted cycloalkyl, —O—(C₁-C₆)alkyl, —O—(C₁-C₆)fluoro-substituted alkyl, —O—(C₃-C₉)cycloalkyl, and —O—(C₃-C₉)fluoro-substituted cycloalkyl, -aryl, —O-aryl, —O—(C₁-C₄)alkyl-aryl, —O—(C₁-C₄)alkyl-heterocycle, and —S(=O)₂—(C₁-C₆)alkyl.

3. The compound of claim 1, wherein Q is selected from the group consisting of 2-chlorophenyl and 3-methoxyphenyl.

4. The compound of claim 1 wherein both V and Z are O.

5. The compound of claim 1 wherein R5 is H.

6. The compound of claim 1 wherein Y is a bond.

7. The compound of claim 6 wherein m is 2.

8. The compound of claim 7 wherein W is —CH₂—.

9. The compound of claim 8 wherein n is 1.

10. The compound of claim 1 wherein U is

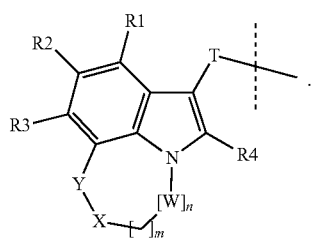

11. The compound of claim 1 wherein T is —CH₂—.

12. The compound of claim 1 wherein T is —C(O)—.

13. The compound of claim 1 wherein U is

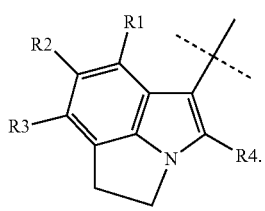

14. The compound of claim 1 wherein U is

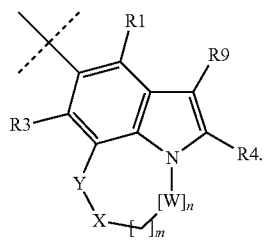

15. The compound of claim 1, wherein the compound is selected from the group consisting of (±)-trans-3-(5,6-dihydro-4H-pyrrolo[3,2,1-ij]quinolin-1-ylmethyl)-4-(1H-indol-3-yl)-pyrrolidine-2,5-dione, (±)-cis-3-(5,6-dihydro-4H-pyrrolo[3,2,1-ij]quinoline-1-carbonyl)-4-(1H-indol-3-yl)-pyrrolidine-2,5-dione, (±)-trans-3-(5,6-dihydro-4H-pyrrolo[3,2,1-ij]quinolin-8-yl)-4-(1H-indol-3-yl)-pyrrolidine-2,5-dione, (±)-trans-3-(5-bromo-1H-indol-3-yl)-4-(5,6-dihydro-4H-pyrrolo[3,2,1-ij]quinolin-8-yl)-pyrrolidine-2,5-dione, (±)-trans-3-(2-Chloro-phenyl)-4-(5,6-dihydro-4H-pyrrolo[3,2,1-ij]quinolin-8-yl)-pyrrolidine-2,5-dione, (±)-trans-3-(5,6-dihydro-4H-pyrrolo[3,2,1-ij]quinolin-8-yl)-4-(3-methoxy-phenyl)-pyrrolidine-2,5-dione, and (±)-trans-3-(4,5-dihydro-pyrrolo[3,2,1-hi]indol-1-yl)-4-(1H-indol-3-yl)-pyrrolidine-2,5-dione.

16. A pharmaceutical composition comprising a compound of formula Ia, Ib, IIa, or IIb as defined in claim 1 or a pharmaceutically acceptable salt thereof together with one or more pharmaceutically acceptable carriers or excipients.

17. The pharmaceutical composition of claim 16 further comprising a chemotherapeutic agent.

18. The pharmaceutical composition of 17, wherein said chemotherapeutic agent is selected from the group consisting of tamoxifen, raloxifene, anastrozole, exemestane, letrozole, trastuzumab, imatanib, paclitaxel, cyclophosphamide, lovastatin, minosine, gemcitabine, arabinofuranosyl cytidine, 5-fluorouracil, methotrexate, docetaxel, goserelin, vincristin, vinblastin, nocodazole, teniposide, etoposide, gemcitabine, epothilone, navelbine, camptothecin, daunonibicin, dactinomycin, mitoxantrone, amsacrine, doxorubicin, epirubicin or idarubicin.

19. A method of treating a cell proliferative disorder, said method comprising administering to a subject in need thereof a therapeutically effective amount of a compound of formula Ia, Ib, IIa, or IIb as defined in claim 1, or a pharmaceutically acceptable salt thereof, in combination with a pharmaceutically acceptable carrier, wherein said cell proliferative disorder is lung cancer, colon cancer, breast cancer, pancreatic cancer, prostate cancer, chronic myelogenous leukemia, melanoma, or ovarian cancer.

20. The method of claim 19, wherein said compound of formula Ia, Ib, IIa, or IIb, or a pharmaceutically acceptable salt thereof, is administered in combination with a chemotherapeutic agent.

21. The method of claim 20, wherein said chemotherapeutic agent is selected from the group consisting of tamoxifen, raloxifene, anastrozole, exemestane, letrozole, trastuzumab, imatanib, paclitaxel, cyclophosphamide, lovastatin, minosine, gemcitabine, arabinofuranosyl cytidine, 5-fluorouracil, methotrexate, docetaxel, goserelin, vincristin, vinblastin, nocodazole, teniposide, etoposide, gemcitabine, epothilone, navelbine, camptothecin, daunonibicin, dactinomycin, mitoxantrone, amsacrine, doxorubicin, epirubicin or idarubicin.

22. The method of claim 19, wherein said treating comprises a reduction in tumor size.

23. The method of claim 19, wherein the cancer is a metastatic cancer.

24. The method of claim 23, wherein said treating comprises inhibition of metastatic cancer cell invasion.

25. The method of claim 19 wherein the cells with said proliferative disorder contains DNA encoding c-Met.

26. The method of claim 25 wherein the cells have a constitutively enhanced c-Met activity.

* * * * *

UNITED STATES PATENT AND TRADEMARK OFFICE
CERTIFICATE OF CORRECTION

PATENT NO. : 8,513,292 B2  Page 1 of 1
APPLICATION NO. : 12/664345
DATED : August 20, 2013
INVENTOR(S) : Neil Westlund et al.

It is certified that error appears in the above-identified patent and that said Letters Patent is hereby corrected as shown below:

In the Claims

Claim 1, Column 68, Lines 56 and 57:

Replace "consisting of H, F, Cl, Br, I, -NR7R8, -(C1-C6) substituted alkyl, -(C3 -C9)cycloalkyl, -(C3-C9) substituted cycloalkyl"

With "consisting of H, F, Cl, Br, I, -NR7R8, -(C1 -C6) alkyl, -(C1-C6) substituted alkyl, -(C3 -C9) cycloalkyl, -(C3-C9) substituted cycloalkyl"

Signed and Sealed this
Thirty-first Day of December, 2013

Margaret A. Focarino
*Commissioner for Patents of the United States Patent and Trademark Office*